United States Patent
Glaenzel et al.

(10) Patent No.: US 9,604,969 B2
(45) Date of Patent: Mar. 28, 2017

(54) PYRIMIDIN-4-YL)OXY)-1H-INDOLE-1-CARBOXAMIDE DERIVATIVES AND USE THEREOF

(71) Applicants: Ulrike Glaenzel, Basel (CH); Robert Nufer, Basel (CH)

(72) Inventors: Ulrike Glaenzel, Basel (CH); Robert Nufer, Basel (CH)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/891,674

(22) PCT Filed: May 16, 2014

(86) PCT No.: PCT/IB2014/061484
§ 371 (c)(1),
(2) Date: Nov. 16, 2015

(87) PCT Pub. No.: WO2014/184778
PCT Pub. Date: Nov. 20, 2014

(65) Prior Publication Data
US 2016/0115156 A1    Apr. 28, 2016

Related U.S. Application Data

(60) Provisional application No. 61/824,464, filed on May 17, 2013.

(51) Int. Cl.
*A01N 43/54*    (2006.01)
*C07D 239/42*    (2006.01)
*C07D 401/04*    (2006.01)
*C07D 403/14*    (2006.01)

(52) U.S. Cl.
CPC .................................. *C07D 403/14* (2013.01)

(58) Field of Classification Search
None
See application file for complete search history.

(56) References Cited

FOREIGN PATENT DOCUMENTS

| WO | 2001/002369 | 1/2001 |
|---|---|---|
| WO | 2010/066684 | 6/2010 |

OTHER PUBLICATIONS

Dubbelman et al., Cancer Chemotherapy and Pharmacology, 79(5):653-663 (2012).
Kimura et al., Biochemical Pharmacology, 34(18):3375-3377 (1985).

*Primary Examiner* — Jared D Barsky
(74) *Attorney, Agent, or Firm* — Joshua Roth

(57) ABSTRACT

This invention relates to certain metabolites of N-(1-methyl-5-(trifluoromethyl)-1H-pyrazol-3-yl)-5-((6-((methylamino)methyl)pyrimidin-4-yl)oxy)-1H-indole-1-carboxamide In particular, the present invention relates to pharmaceutical compositions comprising these metabolites, as well as processes for their preparation and their use in the treatment of diseases.

2 Claims, 6 Drawing Sheets

Figure 1 illustrates the x-ray powder diffraction patterns of N-(1-methyl-5-(trifluoromethyl)-1H-pyrazol-3-yl)-5-((6-((methylamino)methyl)pyrimidin-4-yl)oxy)-1H-indole-1-carboxamide HCl salt Form A.
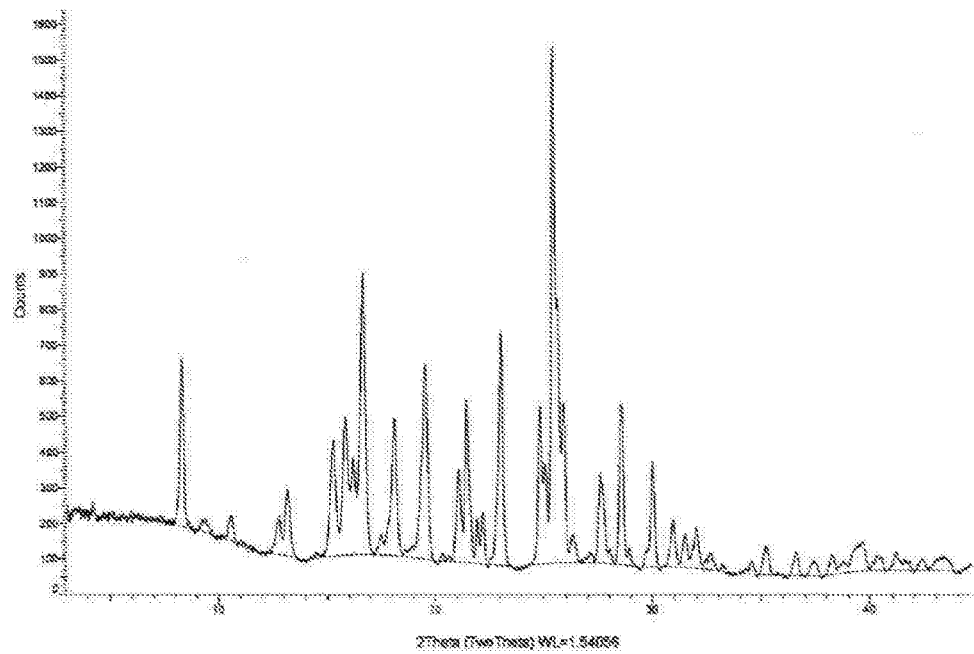

Figure 2 illustrates the differential scanning calorimetry (DSC) of crystalline N-(1-methyl-5-(trifluoromethyl)-1H-pyrazol-3-yl)-5-((6-((methylamino)methyl)pyrimidin-4-yl)oxy)-1H-indole-1-carboxamide HCl salt Form A.
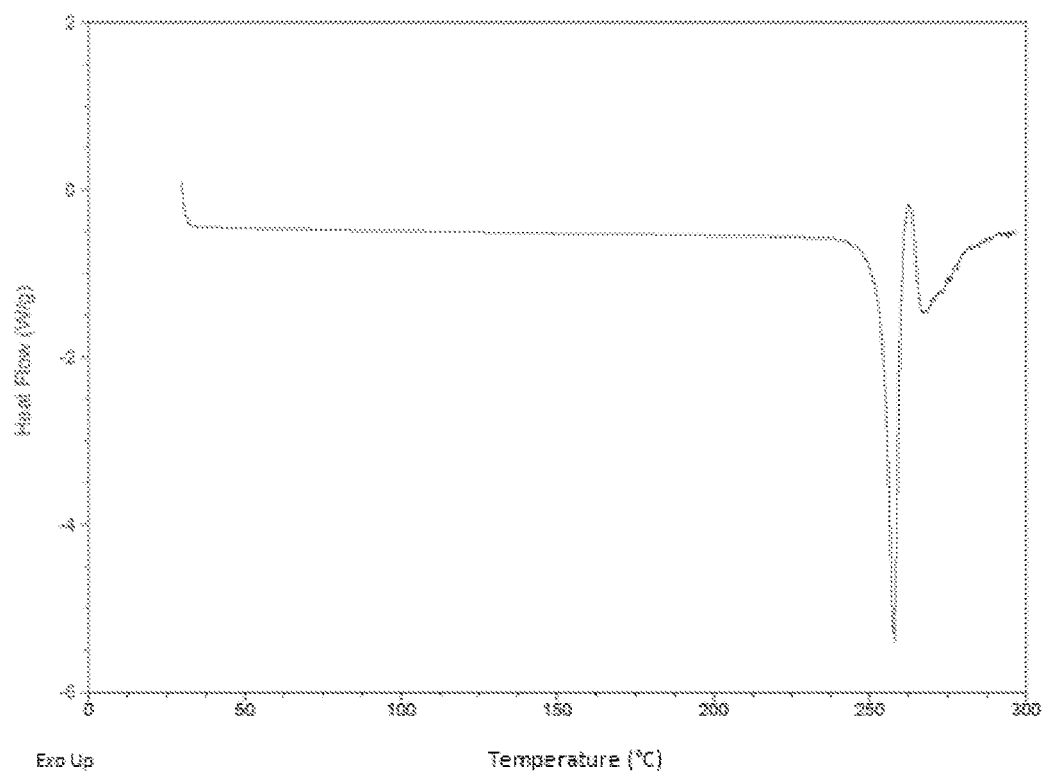

Figure 3 illustrates the x-ray powder diffraction patterns of N-(1-methyl-5-(trifluoromethyl)-1H-pyrazol-3-yl)-5-((6-((methylamino)methyl)pyrimidin-4-yl)oxy)-1H-indole-1-carboxamide HCl salt Form B.
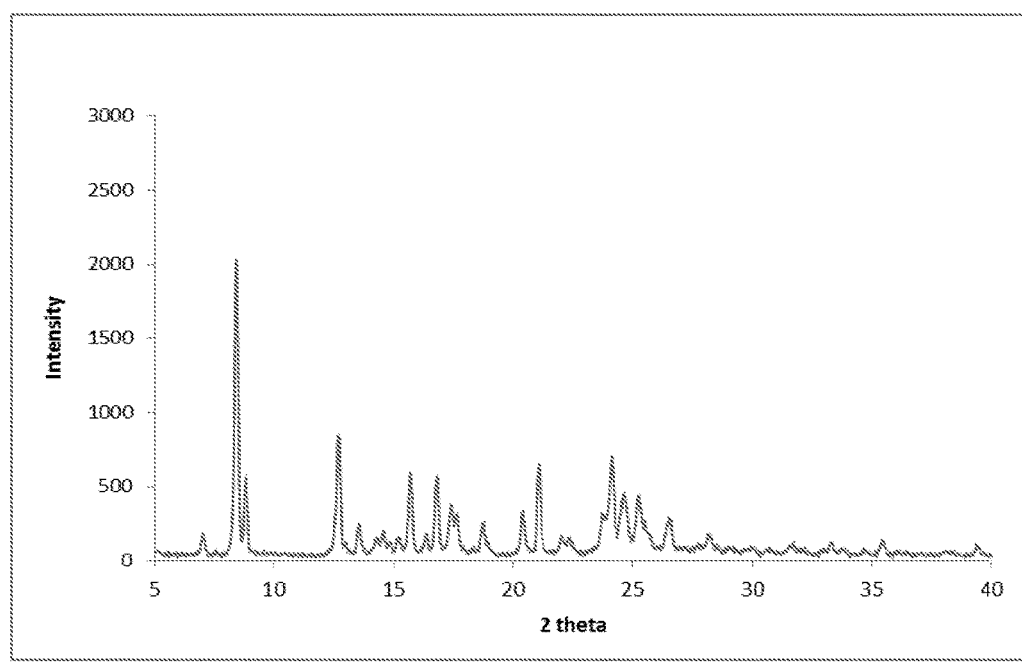

Figure 4 illustrates the differential scanning calorimetry (DSC) of crystalline N-(1-methyl-5-(trifluoromethyl)-1H-pyrazol-3-yl)-5-((6-((methylamino)methyl)pyrimidin-4-yl)oxy)-1H-indole-1-carboxamide HCl salt Form B.
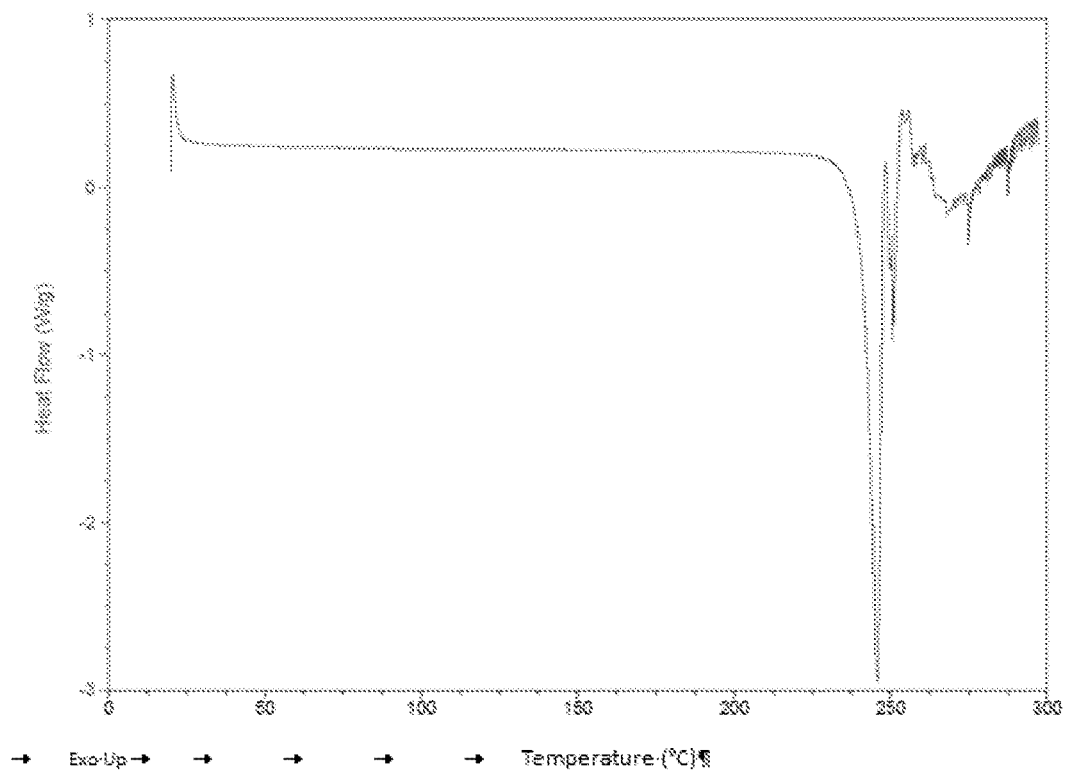

Figure 5 illustrates the x-ray powder diffraction patterns of N-(1-methyl-5-(trifluoromethyl)-1H-pyrazol-3-yl)-5-((6-((methylamino)methyl)pyrimidin-4-yl)oxy)-1H-indole-1-carboxamide Form A.
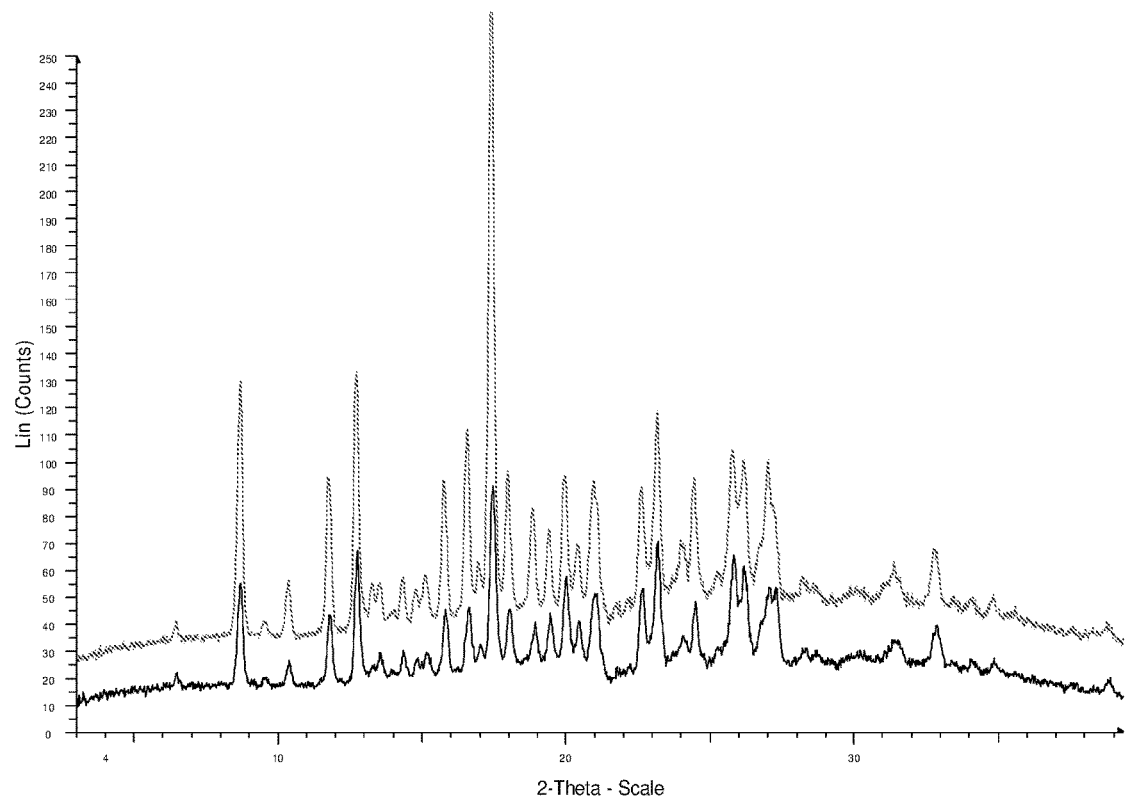

Figure 6 illustrates the differential scanning calorimetry (DSC) of crystalline N-(1-methyl-5-(trifluoromethyl)-1H-pyrazol-3-yl)-5-((6-((methylamino)methyl)pyrimidin-4-yl)oxy)-1H-indole-1-carboxamide Form A.
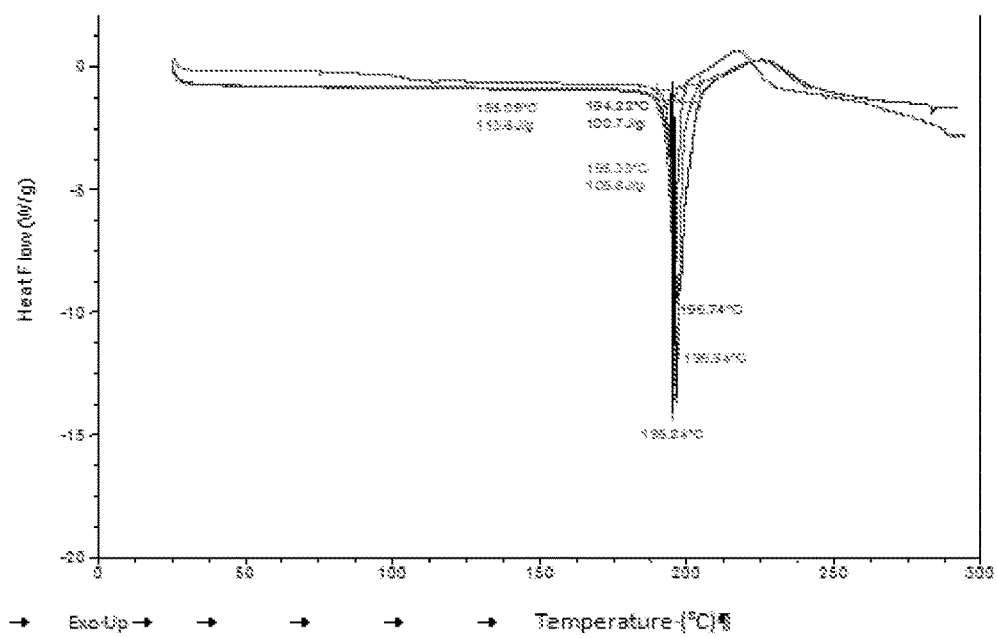

PYRIMIDIN-4-YL)OXY)-1H-INDOLE-1-CARBOXAMIDE DERIVATIVES AND USE THEREOF

This application is a U.S. National Phase filing of International Application No. PCT/IB2014/061484 filed 16 May 2013, which claims priority to U.S. Application No. 61/824,464 filed 17 May 2013, the contents of which are incorporated herein by reference in their entirety.

FIELD OF THE INVENTION

This invention relates to certain analogues of N-(1-methyl-5-(trifluoromethyl)-1H-pyrazol-3-yl)-5-((6-((methylamino)methyl)pyrimidin-4-yl)oxy)-1H-indole-1-carboxamide. In particular, the present invention relates to pharmaceutical compositions comprising these compounds, as well as processes for their preparation and their use in the treatment of conditions mediated by a protein kinase, e.g. VEGF-R receptor dependent diseases.

BACKGROUND OF THE INVENTION

WO2010/066684, the relevant disclosure of which is incorporated herein by reference, discloses a series of Heterobicyclic Carboxamides as inhibitors for kinases. Accordingly, it has now been found that these compounds show inhibition of a number of protein kinases. The compounds, described in WO2010/066684, especially show inhibition of one or more of the following protein kinases: EphB4, c-Abl, Bcr-Abl, c-Kit, Raf kinases such as especially B-Raf, the rearranged during transfection (RET) protooncogene, Platelet-derived Growth Factor Receptors (PDGFRs), Lck, Hck and most especially the Vascular Endothelial Growth Factor Receptors (VEGF-Rs) such as in particular VEGF-R1 and VEGF-R2. The compounds further also inhibit mutants of said kinases. In view of these activities, the compounds described in WO2010/066684 can be used for the treatment of diseases related to especially aberrant or excessive activity of such types of kinases, especially those mentioned. A particular compound in this class is N-(1-methyl-5-(trifluoromethyl)-1H-pyrazol-3-yl)-5-((6-((methylamino)methyl)pyrimidin-4-yl)oxy)-1H-indole-1-carboxamide which may be obtained in the form of the free base or as a hydrochloride salt. The structure of N-(1-methyl-5-(trifluoromethyl)-1H-pyrazol-3-yl)-5-((6-((methylamino)methyl)pyrimidin-4-yl)oxy)-1H-indole-1-carboxamide is shown below:

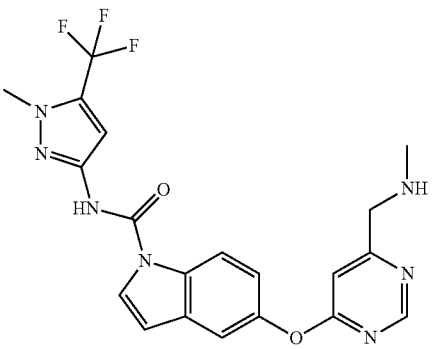

SUMMARY OF THE INVENTION

N-(1-methyl-5-(trifluoromethyl)-1H-pyrazol-3-yl)-5-((6-((methylamino)methyl)pyrimidin-4-yl)oxy)-1H-indole-1-carboxamide is known to be metabolised via metabolic transformations characterized by the following reactions:

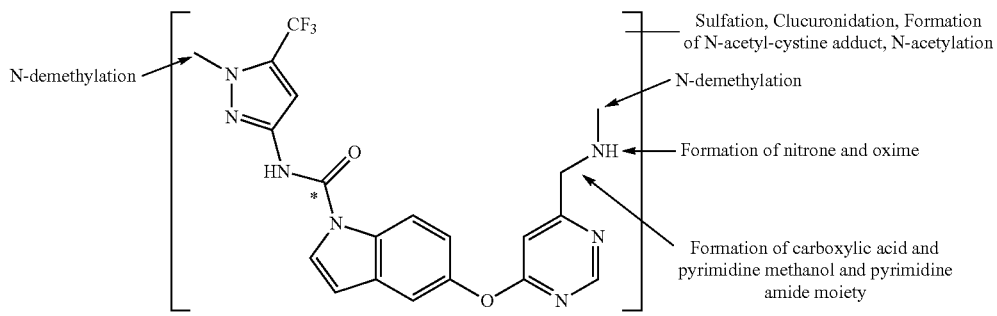

Metabolic reactions include:
  Formation of a nitrone and oxime,
  Formation of a pyrimidin-carboxylic acid and pyrimidin-methanol,
  Formation of a pyrimidin-amide moiety,
  Demethylation of the methyl-5-trifluoromethyl-pyrazol moiety,
  Demethylation of the methylaminomethyl-pyrimidin moiety.
  Forming an N-acetyl-cysteine adduct,
  N-acetylation,
  Sulfation,
  Glucuronidation
  certain additional metabolites are generated through in-vitro and in-vivo metabolism reactions and discussed infra.

Certain analogues of N-(1-methyl-5-(trifluoromethyl)-1H-pyrazol-3-yl)-5-((6-((methylamino)methyl)pyrimidin-4-yl)oxy)-1H-indole-1-carboxamide have now been identified and characterised. These analogues are potential new agents for treatment of ophthalmic diseases, such as Age Related Macular Degeneration.

Therefore, the present invention relates to an isolated form of any metabolite, or salt thereof, of N-(1-methyl-5-(trifluoromethyl)-1H-pyrazol-3-yl)-5-((6-((methylamino)methyl)pyrimidin-4-yl)oxy-1H-indole-1-carboxamide and pharmaceutical compositions, methods of treatment and uses thereof.

The invention further relates to methods of making and/or salts and polymorphs of N-(1-methyl-5-(trifluoromethyl)-

1H-pyrazol-3-yl)-5-((6-((methylamino)methyl)pyrimidin-4-yl)oxy)-1H-indole-1-carboxamide as well as pharmaceutical compositions, methods of treatment and uses thereof.

BRIEF DESCRIPTION OF THE DRAWINGS

FIG. 1. illustrates the x-ray powder diffraction patterns of N-(1-methyl-5-(trifluoromethyl)-1H-pyrazol-3-yl)-5-((6-((methylamino)methyl)pyrimidin-4-yl)oxy)-1H-indole-1-carboxamide HCl salt Form A.

FIG. 2. illustrates the differential scanning calorimetry (DSC) of crystalline N-(1-methyl-5-(trifluoromethyl)-1H-pyrazol-3-yl)-5-((6-((methylamino)methyl)pyrimidin-4-yl)oxy)-1H-indole-1-carboxamide HCl salt Form A.

FIG. 3. illustrates the x-ray powder diffraction patterns of N-(1-methyl-5-(trifluoromethyl)-1H-pyrazol-3-yl)-5-((6-((methylamino)methyl)pyrimidin-4-yl)oxy)-1H-indole-1-carboxamide HCl salt Form B.

FIG. 4. illustrates the differential scanning calorimetry (DSC) of crystalline N-(1-methyl-5-(trifluoromethyl)-1H-pyrazol-3-yl)-5-((6-((methylamino)methyl)pyrimidin-4-yl)oxy)-1H-indole-1-carboxamide HCl salt Form B.

FIG. 5. illustrates the x-ray powder diffraction patterns of N-(1-methyl-5-(trifluoromethyl)-1H-pyrazol-3-yl)-5-((6-((methylamino)methyl)pyrimidin-4-yl)oxy)-1H-indole-1-carboxamide Form A.

FIG. 6. illustrates the differential scanning calorimetry (DSC) of crystalline N-(1-methyl-5-(trifluoromethyl)-1H-pyrazol-3-yl)-5-((6-((methylamino)methyl)pyrimidin-4-yl)oxy)-1H-indole-1-carboxamide Form A.

DISCLOSURE OF THE INVENTION

Thus, the present invention relates to the following Compounds, which are analogues of N-(1-methyl-5-(trifluoromethyl)-1H-pyrazol-3-yl)-5-((6-((methylamino)methyl)pyrimidin-4-yl)oxy)-1H-indole-1-carboxamide formed by the metabolism of N-(1-methyl-5-(trifluoromethyl)-1H-pyrazol-3-yl)-5-((6-((methylamino)methyl)pyrimidin-4-yl)oxy)-1H-indole-1-carboxamide in animals, man and/or in in-vitro cellular assays.

In the compounds below, the box around a part of the compound is labelled "oxygenation" to indicate that somewhere along the length of the indicated region of the compound there is an additional oxygen, e.g. N-oxide or hydroxyl group.

In the compounds below, the box around the compound is labelled "Glucuronide" to indicate that somewhere along the length of the compound there is a transfer of a glucoronic acid to some part of the molecule, i.e. the product is the transfer of the glucuronic acid component of UDP-glucuronic acid to a part of the N-(1-methyl-5-(trifluoromethyl)-1H-pyrazol-3-yl)-5-((6-((methylamino)methyl)pyrimidin-4-yl)oxy)-1H-indole-1-carboxamide molecule.

In the compounds below, the box around the compound is labelled "Sulfation" to indicate that somewhere along the length of the compound there is a transfer of a sulphuric acid to some part of the molecule, i.e. the product is the transfer of sulfuric acid component by PAPS (3'-phospho-adenosine-5'-phosphosulfate) to a part of the N-(1-methyl-5-(trifluoromethyl)-1H-pyrazol-3-yl)-5-((6-((methylamino)methyl) pyrimidin-4-yl)oxy)-1H-indole-1-carboxamide molecule.

Therefore, in a first aspect, the present invention relates to an isolated form of any metabolite, or salt thereof, of N-(1-methyl-5-(trifluoromethyl)-1H-pyrazol-3-yl)-5-((6-((methylamino)methyl)pyrimidin-4-yl)oxy)-1H-indole-1-carboxamide.

In a second embodiment, the invention is the metabolite, or salt thereof, according to the first embodiment, wherein the metabolite is selected from:

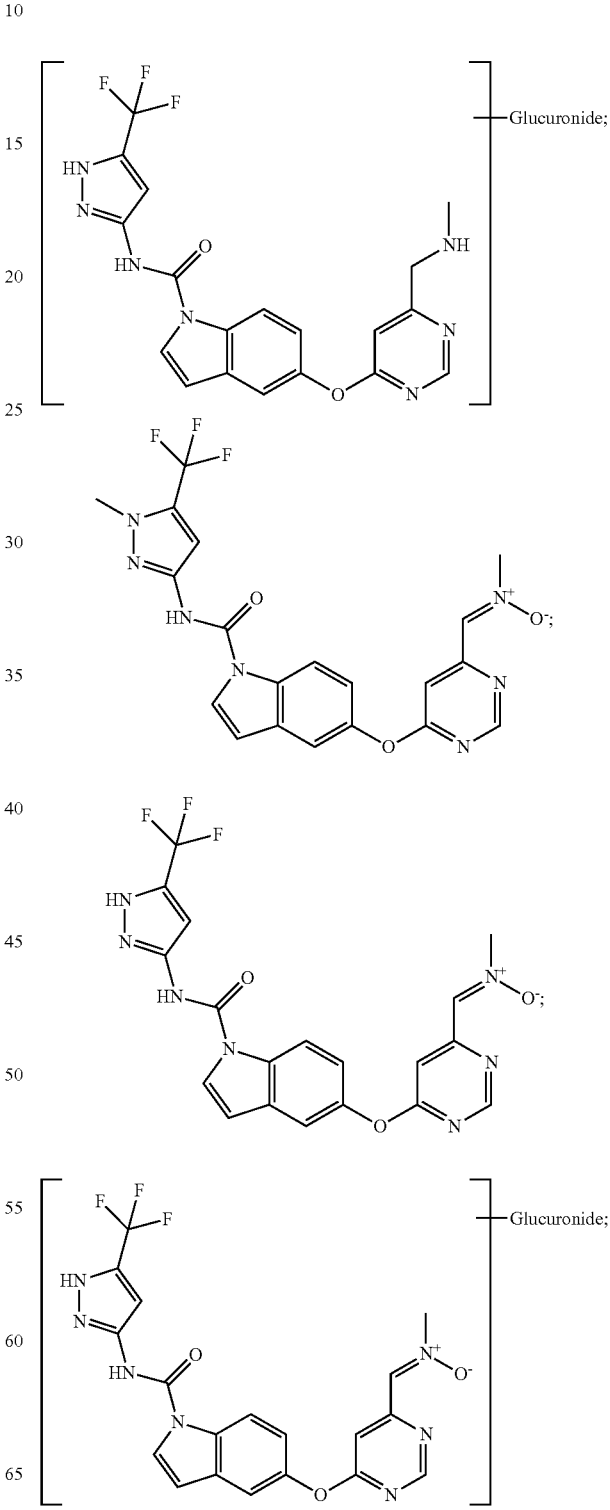

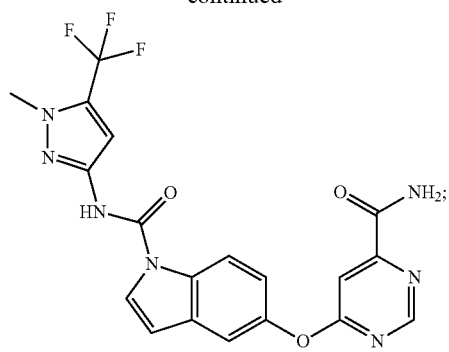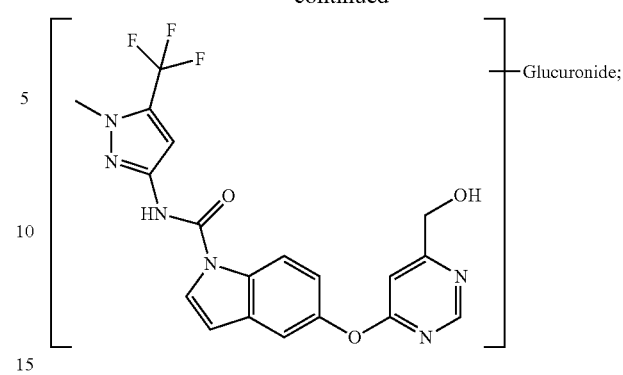

In a third embodiment, the invention is the metabolite, or salt thereof, according to the first embodiment wherein the metabolite is selected from:

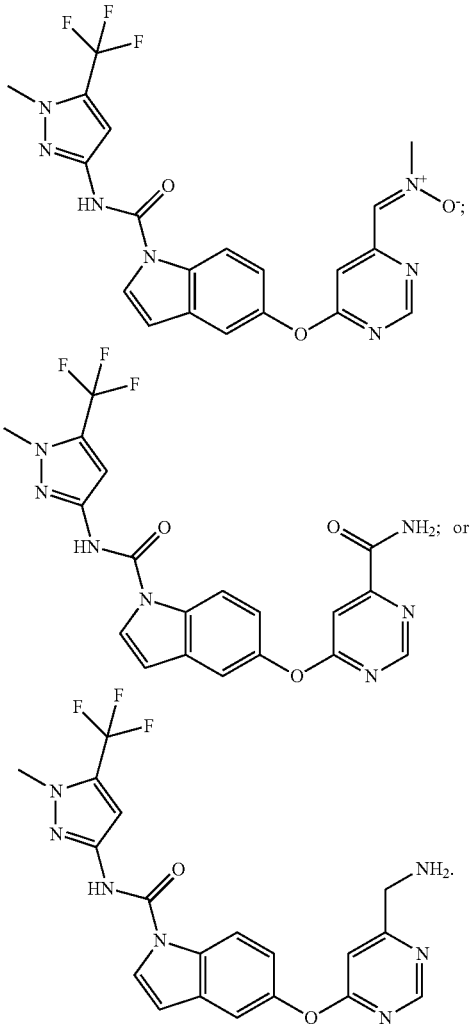

In a fourth embodiment, the invention is the metabolite, or salt thereof, according to the first embodiment wherein the metabolite is:

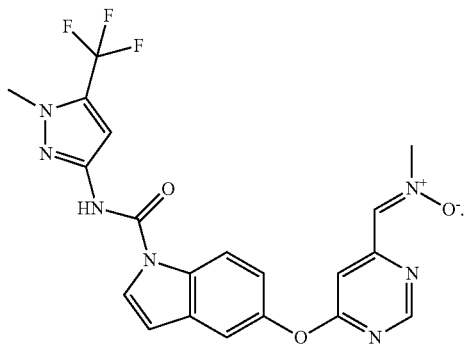

In a fifth embodiment, the invention is a pharmaceutical formulation comprising, the metabolite of the first through fourth embodiment, or a salt thereof, and at least one pharmaceutically acceptable excipient.

In sixth embodiment, the invention is a method of treating an ocular neovascular disease in a patient, the method comprising the step of administering the metabolite of the first through fourth embodiments or a salt thereof to the patient in need of therapy.

In a seventh embodiment, the invention is a use of a metabolite of any one of the first through fourth embodiments, or a salt thereof, for the treatment of a disease or disorder in a subject mediated by a protein kinase, especially protein tyrosine kinase, more especially VEGF-R receptor dependent diseases.

In an eighth embodiment, the invention is the use of a metabolite according to any one of the first through fourth embodiments, for the treatment of a disorder or disease in a subject characterized by an abnormal activity of a protein kinase, especially protein tyrosine kinase, more especially VEGF-R receptor.

In a ninth embodiment, the invention is a method of inhibiting VEGF-R activity in a subject, wherein the method comprises administering to the subject a therapeutically effective amount of the metabolite according to any one of the first through fourth embodiments.

In a tenth embodiment, the invention is a method of treating a disorder or a disease in a subject mediated by VEGF-R, wherein the method comprises administering to the subject a therapeutically effective amount of the metabolite according to any one of the first through fourth embodiments.

In an eleventh embodiment, the invention is the method of the tenth embodiment, wherein the disease is AMD or Diabetic Retinopathy.

In a twelfth embodiment, the invention is a crystalline form of N-(1-methyl-5-(trifluoromethyl)-1H-pyrazol-3-yl)-5-((6-((methylamino)methyl)pyrimidin-4-yl)oxy)-1H-indole-1-carboxamide hydrochloride.

In a thirteenth embodiment, the invention is the crystalline form according to the twelfth embodiment comprising N-(1-methyl-5-(trifluoromethyl)-1H-pyrazol-3-yl)-5-((6-((methylamino)methyl)pyrimidin-4-yl)oxy)-1H-indole-1-carboxamide hydrochloride Form A.

In a fourteenth embodiment, the invention is the crystalline form according to the twelfth or thirteenth embodiments consisting essentially of Form A.

In a fifteenth embodiment, the invention is the crystalline form according to the eleventh through fourteenth, wherein said Form A is in substantially pure form.

In a sixteenth embodiment, the invention is the crystalline form according to the eleventh through fifteenth embodiments characterized by a x-ray powder diffraction pattern comprising four or more 2θ values selected from the group consisting of 6.391±0.2°, 8.6±0.2°, 9.532±0.2°, 10.333±0.2°, 11.74±0.2°, 12.691±0.2°, 13.486±0.2°, 14.767±0.2°, 15.105±0.2°, 15.767±0.2°, 16.571±0.2°, 16.973±0.2°, 17.39±0.2°, 17.986±0.2°, 18.854±0.2°, 19.427±0.2°, 19.99±0.2°, 20.472±0.2°, 20.993±0.2°, 22.593±0.2°, 23.166±0.2°, 24.012±0.2°, 24.413±0.2°, 25.212±0.2°, 25.788±0.2°, 26.174±0.2°, 26.974±0.2°, 27.245±0.2°, 28.231±0.2°, 32.809±0.2°, 34.843±0.2° and 38.831±0.2° at a temperature of about 22° C.

In a seventeenth embodiment, the invention is the crystalline form of the sixteenth embodiment further characterized by a x-ray powder diffraction pattern comprising five or more 2θ values selected from the group consisting of 6.391±0.2°, 8.6±0.2°, 9.532±0.2°, 10.333±0.2°, 11.74±0.2°, 12.691±0.2°, 13.486±0.2°, 14.767±0.2°, 15.105±0.2°, 15.767±0.2°, 16.571±0.2°, 16.973±0.2°, 17.39±0.2°, 17.986±0.2°, 18.854±0.2°, 19.427±0.2°, 19.99±0.2°, 20.472±0.2°, 20.993±0.2°, 22.593±0.2°, 23.166±0.2°, 24.012±0.2°, 24.413±0.2°, 25.212±0.2°, 25.788±0.2°, 26.174±0.2°, 26.974±0.2°, 27.245±0.2°, 28.231±0.2°, 32.809±0.2°, 34.843±0.2° and 38.831±0.2° at a temperature of about 22° C.

In an eighteenth embodiment, the invention is a crystalline form of N-(1-methyl-5-(trifluoromethyl)-1H-pyrazol-3-yl)-5-((6-((methylamino)methyl)pyrimidin-4-yl)oxy)-1H-indole-1-carboxamide hydrochloride having a X-ray diffraction spectrum substantially the same as the X-ray powder diffraction spectrum shown in FIG. 1.

In a nineteenth embodiment, the invention is a crystalline form of N-(1-methyl-5-(trifluoromethyl)-1H-pyrazol-3-yl)-5-((6-((methylamino)methyl)pyrimidin-4-yl)oxy)-1H-indole-1-carboxamide hydrochloride having a differential scanning calorimetry (DSC) thermogram substantially the same as that shown in shown in FIG. 2.

In a twentieth embodiment, the invention is a pharmaceutical composition comprising the crystalline form according to the eleventh through nineteenth embodiments and a pharmaceutically acceptable carrier or diluent.

In a twentyfirst embodiment, the invention is the pharmaceutical composition according to the twentieth embodiment wherein said crystalline form is Form A.

In a twentysecond embodiment, the invention is the pharmaceutical composition according to the twentyfirst embodiment wherein said Form A is in substantially pure form.

In a twentythird embodiment, the invention is a combination, in particular a pharmaceutical combination, comprising a therapeutically effective amount of the crystalline from according to any one of the eleventh through nineteenth embodiments and a second therapeutically active agent.

In a twentyfourth embodiment, the invention is the pharmaceutical composition according to the twentythird embodiment wherein said crystalline form is Form A.

In a twentyfifth embodiment, the invention is the pharmaceutical composition according to the twentyfourth embodiment wherein said Form A is in substantially pure form.

In a twentysixth embodiment, the invention is a method of treating a disorder or a disease in a subject mediated by VEGF-R, comprising administering to the mammal a therapeutically-effective amount of a crystalline form of N-(1-methyl-5-(trifluoromethyl)-1H-pyrazol-3-yl)-5-((6-((methylamino)methyl)pyrimidin-4-yl)oxy)-1H-indole-1-carboxamide hydrochloride according to the eleventh through nineteenth embodiments.

In a twentyseventh embodiment, the invention is the method according to the twentysixth embodiment wherein said crystalline form is Form A.

In a twentyeighth embodiment, the invention is the method according to the twentyseventh embodiment wherein said Form A is in substantially pure form.

In a twentyninth embodiment, the invention is the method according to the twenty sixth embodiment, wherein the subject is a human.

In a thirtieth embodiment, the invention is a composition comprising at least 90 weight % of the crystalline form according to the eleventh through nineteenth embodiments, based on the weight of the composition.

In a thirtyfirst embodiment, the invention is process of making Form A of N-(1-methyl-5-(trifluoromethyl)-1H-pyrazol-3-yl)-5-((6-((methylamino)methyl)pyrimidin-4-yl)oxy)-1H-indole-1-carboxamide hydrochloride comprising the steps of Example 5.

In a thirtysecond embodiment, the invention is the crystalline form according to the twelfth embodiment comprising N-(1-methyl-5-(trifluoromethyl)-1H-pyrazol-3-yl)-5-((6-((methylamino)methyl)pyrimidin-4-yl)oxy)-1H-indole-1-carboxamide hydrochloride Form B.

In a thirtythird embodiment, the invention is the crystalline form according to the twelfth or thirtysecond embodiments consisting essentially of Form B.

In a thirtyfourth embodiment, the invention is the crystalline form according to the thirty second to thirtythird embodiments, wherein said Form B is in substantially pure form.

In a thirtyfifth embodiment, the invention is the crystalline form according to the twelfth or thirtysecond to thirtyfourth embodiments characterized by a x-ray powder diffraction pattern comprising four or more 2θ values selected from the group consisting of 8.4113±0.2°, 8.836±0.2°, 12.6789±0.2°, 13.5686±0.2°, 15.7124±0.2°, 16.8248±0.2°, 17.3911±0.2°, 18.7462±0.2°, 20.4248±0.2°, 21.072±0.2°, 24.126±0.2°, 24.6518±0.2°, 25.2788±0.2°, 26.5327±0.2°, 27.726±0.2° and 35.4721±0.2°, at a temperature of about 22° C.

In a thirtysixth embodiment, the invention is the crystalline form according to the thirtyfifth embodiment further characterized by a x-ray powder diffraction pattern comprising five or more 2θ values selected from the group consisting of 8.4113±0.2°, 8.836±0.2°, 12.6789±0.2°, 13.5686±0.2°, 15.7124±0.2°, 16.8248±0.2°, 17.3911±0.2°, 18.7462±0.2°, 20.4248±0.2°, 21.072±0.2°, 24.126±0.2°, 24.6518±0.2°, 25.2788±0.2°, 26.5327±0.2°, 27.726±0.2° and 35.4721±0.2°, at a temperature of about 22° C.

In a thirtyseventh embodiment, the invention is a crystalline form of N-(1-methyl-5-(trifluoromethyl)-1H-pyrazol-3-yl)-5-((6-((methylamino)methyl)pyrimidin-4-yl)oxy)-1H-indole-1-carboxamide hydrochloride having a X-ray diffraction spectrum substantially the same as the X-ray powder diffraction spectrum shown in FIG. 3.

In a thirtyeighth embodiment, the invention is a crystalline form of N-(1-methyl-5-(trifluoromethyl)-1H-pyrazol-3-yl)-5-((6-((methylamino)methyl)pyrimidin-4-yl)oxy)-1H-indole-1-carboxamide hydrochloride having a differential scanning calorimetry (DSC) thermogram substantially the same as that shown in shown in FIG. 4.

In a thirtyninth embodiment, the invention is a pharmaceutical composition comprising the crystalline form according to twelfth or thirtysecond through thirtyeighth embodiments and a pharmaceutically acceptable carrier or diluent.

In a fortieth embodiment, the invention is the pharmaceutical composition according to the thirtyninth embodiment wherein said crystalline form is Form B.

In a fortyfirst embodiment, the invention is the pharmaceutical composition according to the fortieth embodiment wherein said Form B is in substantially pure form.

In a fortysecond embodiment, the invention is a combination, in particular a pharmaceutical combination, comprising a therapeutically effective amount of the crystalline from according to any one of the twelfth or thirtysecond to thirtyeighth embodiments and a second therapeutically active agent.

In a fortythird embodiment, the invention is the pharmaceutical composition according to the fortysecond embodiment wherein said crystalline form is Form B.

In a fortyfourth embodiment, the invention is the pharmaceutical composition according to the fortythird embodiment wherein said Form B is in substantially pure form.

In a fortyfifth embodiment, the invention is a method of treating a disorder or a disease in a subject mediated by VEGF-R, comprising administering to the mammal a therapeutically-effective amount of a crystalline form of N-(1-methyl-5-(trifluoromethyl)-1H-pyrazol-3-yl)-5-((6-((methylamino)methyl)pyrimidin-4-yl)oxy)-1H-indole-1-carboxamide hydrochloride according to the twelfth or thirtysecond to thirtyeighth embodiments.

In a fortysixth embodiment, the invention is the method according to the fortyfifth embodiment wherein said crystalline form is Form B.

In fortyseventh embodiment, the invention is the method according to the fortysixth embodiment wherein said Form B is in substantially pure form.

In a fortyeighth embodiment, the invention is the method according to the fortyfifth embodiment, wherein the subject is a human.

In a fortyninth embodiment, the invention is a composition comprising at least 90 weight % of the crystalline form according to the twelfth or thirtysecond to thirtyeighth embodiments, based on the weight of the composition.

In a fiftieth embodiment, the invention is a process of making Form B of N-(1-methyl-5-(trifluoromethyl)-1H-pyrazol-3-yl)-5-((6-((methylamino)methyl)pyrimidin-4-yl)oxy)-1H-indole-1-carboxamide hydrochloride comprising the steps of Example 6.

In a fiftyfirst embodiment, the invention is a crystalline form of N-(1-methyl-5-(trifluoromethyl)-1H-pyrazol-3-yl)-5-((6-((methylamino)methyl)pyrimidin-4-yl)oxy)-1H-indole-1-carboxamide.

In a fiftysecond embodiment, the invention is the crystalline form according to the fiftyfirst embodiment comprising N-(1-methyl-5-(trifluoromethyl)-1H-pyrazol-3-yl)-5-((6-((methylamino)methyl)pyrimidin-4-yl)oxy)-1H-indole-1-carboxamide Form A.

In a fiftythird embodiment, the invention is the crystalline form according to the fiftyfirst or fiftysecond embodiments consisting essentially of Form A.

In a fiftyfourth embodiment, the invention is the crystalline form according to the fiftyfirst through fiftythird embodiments, wherein said Form A is in substantially pure form.

In a fiftyfifth embodiment, the invention is the crystalline form according to the fiftyfirst through fiftyfourth embodiments is characterized by a x-ray powder diffraction pattern comprising four or more 2θ values selected from the group consisting of 8.664±0.2°, 16.595±0.2°, 17.423±0.2°, 18.017±0.2°, 19.448±0.2°, 20.002±0.2°, 20.468±0.2°, 21.071±0.2°, 22.649±0.2°, 23.215±0.2°, 24.468±0.2° and 25.839±0.2°, at a temperature of about 22° C.

In a fiftysixth embodiment, the invention is the crystalline form according to the fiftyfifth embodiment further characterized by a x-ray powder diffraction pattern comprising five or more 2θ values selected from the group consisting of 8.664±0.2°, 16.595±0.2°, 17.423±0.2°, 18.017±0.2°, 19.448±0.2°, 20.002±0.2°, 20.468±0.2°, 21.071±0.2°, 22.649±0.2°, 23.215±0.2°, 24.468±0.2° and 25.839±0.2°, at a temperature of about 22° C.

In a fiftyseventh embodiment, the invention is a crystalline form of N-(1-methyl-5-(trifluoromethyl)-1H-pyrazol-3-yl)-5-((6-((methylamino)methyl)pyrimidin-4-yl)oxy)-1H-indole-1-carboxamide having a X-ray diffraction spectrum substantially the same as the X-ray powder diffraction spectrum shown in FIG. 5.

In a fiftyeighth embodiment, the invention is a crystalline form of N-(1-methyl-5-(trifluoromethyl)-1H-pyrazol-3-yl)-5-((6-((methylamino)methyl)pyrimidin-4-yl)oxy)-1H-indole-1-carboxamide having a differential scanning calorimetry (DSC) thermogram substantially the same as that shown in shown in FIG. 6.

In a fiftyninth embodiment, the invention is a pharmaceutical composition comprising the crystalline form according to the fiftyfirst through fiftyeighth embodiments and a pharmaceutically acceptable carrier or diluent.

In a sixtieth embodiment, the invention is the pharmaceutical composition according to the fiftyninth embodiment wherein said crystalline form is Form A.

In a sixtyfirst embodiment, the invention is the pharmaceutical composition according to the sixtieth embodiment wherein said Form A is in substantially pure form.

In a sixtysecond embodiment, the invention is a combination, in particular a pharmaceutical combination, comprising a therapeutically effective amount of the crystalline from according to any one of fiftyfirst through fiftyeighth embodiments and a second therapeutically active agent.

In a sixtythird embodiment, the invention is the pharmaceutical composition according to the sixtysecond embodiment wherein said crystalline form is Form A.

In a sixtyfourth embodiment, the invention is the pharmaceutical composition according to sixtythird embodiment wherein said Form A is in substantially pure form.

In a sixtyfifth embodiment, the invention is a method of treating a disorder or a disease in a subject mediated by VEGF-R, comprising administering to the mammal a therapeutically-effective amount of a crystalline form of N-(1-methyl-5-(trifluoromethyl)-1H-pyrazol-3-yl)-5-((6-((methylamino)methyl)pyrimidin-4-yl)oxy)-1H-indole-1-carboxamide according to fiftyfirst through fiftyeighth embodiments.

In a sixtysixth embodiment, the invention is the method according to the sixtyfifth embodiment wherein said crystalline form is Form A.

In a sixtyseventh embodiment, the invention is the method according to the sixtysixth embodiment wherein said Form A is in substantially pure form.

In a sixtyeighth embodiment, the invention is the method according to the sixtyfifth embodiment, wherein the subject is a human.

In a sixtyninth embodiment, the invention is a composition comprising at least 90 weight % of the crystalline form according to fiftyfirst through fiftyeighth embodiments, based on the weight of the composition.

In a seventieth embodiment, the invention is a process of making Form A of N-(1-methyl-5-(trifluoromethyl)-1H-pyrazol-3-yl)-5-((6-((methylamino)methyl)pyrimidin-4-yl)oxy)-1H-indole-1-carboxamide hydrochloride comprising the steps of Example 7.

In a seventyfirst embodiment, the invention is a process of making N-(1-methyl-5-(trifluoromethyl)-1H-pyrazol-3-yl)-5-((6-((methylamino)methyl)pyrimidin-4-yl)oxy)-1H-indole-1-carboxamide according to Example 8.

By "isolated form" we mean that the compound is free from any of the components that would normally accompany it when it is formed metabolically in vivo. For example, it is free of any biological matter, such as serum components, as well as other metabolites of N-(1-methyl-5-(trifluoromethyl)-1H-pyrazol-3-yl)-5-((6-((methylamino)methyl)pyrimidin-4-yl)oxy)-1H-indole-1-carboxamide formed in vivo. Suitably, the compound is in a purified and isolated form. By "purified" we mean that the compound is conveniently greater that 75% pure, more conveniently greater than 90% pure, and preferably greater than 95% pure and most preferably greater than 98% pure.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the term "pharmaceutically acceptable salts" refers to salts that retain the biological effectiveness and properties of the compounds of this invention and, which are not biologically or otherwise undesirable. In many cases, the compounds of the present invention are capable of forming acid and/or base salts by virtue of the presence of amino and/or carboxyl groups or groups similar thereto. Pharmaceutically acceptable acid addition salts can be formed with inorganic acids and organic acids, e.g., acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts. Inorganic acids from which salts can be derived include, for example, hydrochloric acid, hydrobromic acid, sulfuric acid, nitric acid and phosphoric acid. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, and aluminum; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, and basic ion exchange resins, specifically such as isopropylamine, trimethylamine, diethylamine, triethylamine, tripropylamine, and ethanolamine. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

The present invention includes all pharmaceutically acceptable isotopically-labeled compounds of the invention, i.e. compounds of the first through seventieth embodiments, wherein (1) one or more atoms are replaced by atoms having the same atomic number, but an atomic mass or mass number different from the atomic mass or mass number usually found in nature, and/or (2) the isotopic ratio of one or more atoms is different from the naturally occurring ratio.

Examples of isotopes suitable for inclusion in the compounds of the invention comprises isotopes of hydrogen, such as $^{2}$H and $^{3}$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labeled compounds of the first through seventieth embodiments, for example, those incorporating a radioactive isotope, are useful in drug and/or substrate tissue distribution studies. The radioactive isotopes tritium, i.e. $^{3}$H, and carbon-14, i.e. $^{14}$C, are particularly useful for this purpose in view of their ease of incorporation and ready means of detection.

Substitution with heavier isotopes such as deuterium, i.e. $^{2}$H, may afford certain therapeutic advantages resulting from greater metabolic stability, for example, increased in vivo half-life or reduced dosage requirements, and hence may be preferred in some circumstances. In certain compounds of the first through seventieth embodiments, residues $R_9$ or the ring formed by the combination of $R_8$ and $R_9$ may comprise one or more deuterium atoms to improve metabolic stability of the compound in vivo.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of the first through seventieth embodiments can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of the first through seventieth embodiments that contain groups capable of acting as donors and/or acceptors for hydrogen bonds may be capable of forming co-crystals with suitable co-crystal formers. These co-crystals may be prepared from compounds of the first through seventieth embodiments by known co-crystal forming procedures. Such procedures include grinding, heating, co-subliming, co-melting, or contacting in solution compounds of the first through seventieth embodiments with the co-crystal former under crystallization conditions and isolating co-crystals thereby formed. Suitable co-crystal formers include those described in WO 2004/078163. Hence the invention further provides co-crystals comprising a compound of the first through seventieth embodiments.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by VEGF or a receptor thereof, or (ii) associated with VEGF activity or the activity of a VEGF receptor, or (iii) characterized by abnormal activity of VEGF or a receptor thereof; or (2) reducing or inhibiting the activity of VEGF or a receptor thereof; or (3) reducing or inhibiting the expression of VEGF or a receptor thereof. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of VEGF or a receptor thereof; or at least partially reducing or inhibiting the expression of VEGF or a receptor thereof. The meaning of the term "a therapeutically effective amount" as illustrated in the above embodiment for VEGF or a receptor thereof applies by the same means to any other relevant proteins/peptides/enzymes, such as Ret, PDGFR alpha and beta, and ckit.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "inhibition" or "inhibiting" refers to the reduction or suppression of a given condition, symptom, or disorder, or disease, or a significant decrease in the baseline activity of a biological activity or process.

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or disubstituted lower alkyl esters, such as the -(amino, mono- or di-lower alkylamino, carboxy, lower alkoxycarbonyl)-lower alkyl esters, the -(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Furthermore, the compounds of the present invention, including their salts, can also be obtained in the form of their hydrates, or include other solvents used for their crystallization.

In another aspect, the present invention provides a pharmaceutical composition comprising a compound of the present invention and a carrier, e.g., a pharmaceutically acceptable carrier. The pharmaceutical composition can be formulated for particular routes of administration such as oral administration, ophthalmic administration (e.g., topical administration, intravitreal injection, implant (including intravitreal, transscleral, sub-Tenon, and the like, depot or the like), and parenteral administration, etc. In addition, the pharmaceutical compositions of the present invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers etc.

Typically, the pharmaceutical compositions are tablets and gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Certain injectable compositions include ocular implants and ocular depot formulations which are suitable for intraocular, periocular, subconjunctival and/or sub-tenon administration. Typically injectable compositions comprise a compound of the first through seventieth embodiments, in combination with a biocompatible or biodegradable polymeric material.

Suitable compositions for transdermal application include an effective amount of a compound of the invention with carrier. Carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin. Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for ocular application, e.g., for the treatment of ocular disease, e.g., for prophylactic or therapeutic use in the treatment of macular degeneration, diabetic retinopathy, rubeosis iridis, neovascularization of the cornea, sclera, retina or other ocular tissue and the like. They are thus particularly suited for use in topical formulations well-known in the art. Such may contain solubilizers, stabilizers, tonicity enhancing agents, buffers and preservatives.

Certain suitable topical eye drop formulations comprise an aqueous solution or aqueous suspension of a compound of the first through seventieth embodiments, optionally further comprising one or more preservatives, tonicity agents, and/or lubricants. As used herein a topical application may also pertain to an inhalation or to an intranasal application. They are conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Ophthalmic compositions of the present invention are formulated so as to be compatible with the eye and/or other tissues to be treated with the compositions. For topical application to the eye, the compositions of the present invention will generally be formulated as sterile aqueous compositions (e.g., suspensions, solutions, emulsions or the like) and typically include at least 70 w/v %, more typically 80 w/v % and even more typically at least 90 or 95 w/v % purified water. The compositions can include any combination of the followings ingredients: one or more preservative [s] (e.g., polymeric quaternary ammonium compound), one or more surfactant[s] (e.g., polysorbate, tyloxapol, polyethoxylated castor oil, combinations thereof or the like), one or more viscosity agent[s] (e.g., substituted cellulose, galactomannan polymer, carboxyvinyl polymer, combinations thereof or the like), one or more buffer[s] (e.g., borate), one or more tonicity agent[s] (e.g., sodium chloride), one or more polyol[s] (e.g., propylene glycol, glycerin, sorbitol, mannitol, combinations thereof or the like) or other suitable ingredients. The ophthalmic compositions intended for direct application to the corneal surface of the eye will be formulated so as to have a pH and tonicity that are compatible with the eye. The compositions will typically have a pH in the range of 4 to 9, preferably 5.5 to 8.5, and most preferably 5.5 to 8.0. Particularly desired pH ranges are 6.0 to 7.8 and more specifically 6.4 to 7.6. The compositions will have an osmolality of 200 to 400 or 450 milliosmoles per kilogram (mOsm/kg), more preferably 240 to 360 mOsm/kg. Further, the ophthalmic compositions suitable for multi-dose topical application are often disposed in an eye dropper, which can dispense individual drops to the corneal surface of the eye.

The present invention further provides anhydrous pharmaceutical compositions and dosage forms comprising the compounds of the present invention as active ingredients, since water may facilitate the degradation of certain compounds. Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds of the invention in free form or in pharmaceutically acceptable salt form, exhibit valuable pharmacological properties, e.g. VEGF receptor modulating properties, e.g. as indicated in in vitro and in vivo tests as provided in the next sections and are therefore indicated for therapy.

Based on the property of the compounds of the first through seventieth embodiments as potent VEGF receptor inhibitors, the compounds of the first through seventieth embodiments are especially suitable for the treatment of diseases associated with deregulated angiogenesis, especially diseases caused by ocular neovascularisation, especially retinopathies such as diabetic retinopathy or age-related macular degeneration, rubeosis iridis, psoriasis, Von Hippel Lindau disease, hemangioblastoma, angioma, mesangial cell proliferative disorders such as chronic or acute renal diseases, e.g. diabetic nephropathy, malignant nephrosclerosis, thrombotic microangiopathy syndromes or transplant rejection, or especially inflammatory renal disease, such as glomerulonephritis, especially mesangioproliferative glomerulonephritis, haemolytic-uraemic syndrome, diabetic nephropathy, hypertensive nephrosclerosis, atheroma, arterial restenosis, autoimmune diseases, acute inflammation, fibrotic disorders (e.g. hepatic cirrhosis), diabetes, endometriosis, chronic asthma, arterial or post-transplantational atherosclerosis, neurodegenerative disorders, and especially neoplastic diseases (especially solid tumours but also leukemias), such as especially breast cancer, adenocarcinoma, colorectal cancer, lung cancer (especially non-small-cell lung cancer), renal cancer, liver cancer, pancreatic cancer, ovarian cancer or cancer of the prostate as well as myeloma, especially multiple myeloma, myelodysplastic syndrome, AML (acute myeloid leukemia), AMM (agnogenic myeloid metaplasia), mesothelioma, glioma and glioblastoma. A compound of the first through seventieth embodiments, is especially suited also to preventing the metastatic spread of tumours and the growth of micrometastases.

Thus, as a further embodiment, the present invention provides the use of a compound of the first through seventieth embodiments in therapy. In a further embodiment, the therapy is selected from a disease which is ameliorated by inhibition of VEGF receptor activity. In another embodiment, the disease is selected from the aforementioned list, suitably ocular diseases, more suitably wet and dry age-related macular degeneration, geographic atrophy, central serous retinopathy, cystoid macular edema, diabetic retinopathy, proliferative diabetic retinopathy, diabetic macular edema, rubeosis iridis, Retinopathy of prematurity, Central and branch retinal vein occlusions, Inflammatory/infectious retinal neovascularization/edema (e.g. posterior uveitis, sarcoid, toxoplasmosis, histoplasmosis, Vogt-Koyanagi-Harada Disease, chronic uveitis, tuberculsosis, syphyllis, punctate and multifocal inner choroidopathy), retinoblastoma, melanoma, ocular tumors, retinal detachment, myopic neovascularization, angiod streaks, Eales disease, ischemic retinopathy (Retinal artery occlusion, Takayasu's, carotid artery occlusion), choroidal rupture, contact lens wear, dry eye, blepharitis, corneal dystrophies, Trauma and previous surgery to the cornea (corneal grafts, LASIK, LASEK), corneal infections (bacterial, viral, parasitic, herpetic), corneal burns (chemical, alkali, acid), corneal graft rejection, Immunological corneal disease (pemhigoid, stevens-Johnsons syndrome), and degenerative corneal diseases.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

In other embodiments, a pharmaceutical composition is provided which comprises at least one compound according to the first through seventieth embodiments and at least one carrier.

A compound of the first through seventieth embodiments may also be used to advantage in combination with other antiproliferative agents. Such antiproliferative agents include, but are not limited to aromatase inhibitors; antiestrogens; topoisomerase I inhibitors; topoisomerase II inhibitors; microtubule active agents; alkylating agents; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; agents used in the treatment of hematologic malignancies; compounds which target, decrease or inhibit the activity of Flt-3; Hsp90 inhibitors; temozolomide (TEMODAL®); and leucovorin.

A compound of the first through seventieth embodiments may also be used to advantage in combination with other ophthalmic therapeutics including but not limited to Macugen, VEGF trap, photodynamic therapy, anecortave Acetate, Steroids, non-steroidal anti-inflammatory (e.g. Naproxen, ibuprofen, diclofenac) Cox-1 and Cox-2 inhibitors, cyclosporine, dexamethasone, mtor (mammalian target of rapamycin) inhibitors such as rapamycin, everolimus, and the like, PKC (protein kinase C) beta inhibitors, Tumor necrosis alpha inhibitors, interleukin one beta inhibitors, platelet derived growth factor beta and alpha and receptors inhibitors, Lucentis®, Avastin, Eylea, VEGF antibodies, PLGF antibodies, siRNA against VEGF family (A-E, PLGF, neuropilin)/VEGF receptors, complement inhibitors targeting classical, alternative and lectin pathways, IL-10 inhibitors, C5aR inhibitors, C3aR inhibitors, and inhibitors of sphingosine phosphate and receptors. The compound of the present invention may be administered either simultaneously with, or before or after, at least one other therapeutic agent. The compound of the present invention may be administered separately, by the same or different route of administration, or together in the same pharmaceutical composition.

In one embodiment, the other therapeutic agent is selected from:

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane can be administered, e.g., in the form as it is marketed, e.g. under the trademark AROMASIN. Formestane can be administered, e.g., in the form as it is marketed, e.g. under the trademark LENTARON. Fadrozole can be administered, e.g., in the form as it is marketed, e.g. under the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Aminoglutethimide can be administered, e.g., in the form as it is marketed, e.g. under the trademark ORIMETEN. A combination of the invention comprising a chemotherapeutic agent which is an aromatase inhibitor is particularly useful for the treatment of hormone receptor positive tumors, e.g. breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX. Raloxifene hydrochloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an antiestrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide (CASODEX), which can be formulated, e.g. as disclosed in U.S. Pat. No. 4,636,505.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topotecan, gimatecan, irinotecan, camptothecin and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the anthracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active agent" relates to microtubule stabilizing, microtubule destabilizing agents and microtublin polymerization inhibitors including, but not limited to taxanes, e.g. paclitaxel and docetaxel, vinca alkaloids, e.g., vinblastine, especially vinblastine sulfate, vincristine, especially vincristine sulfate, and vinorelbine, discodermolides, cochicine and epothilones and derivatives thereof, e.g. epothilone B or D or derivatives thereof. Paclitaxel may be administered e.g. in the form as it is marketed, e.g. TAXOL. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R.P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating agent" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g. under the trademark HOLOXAN.

The term "histone deacetylase inhibitors" or "HDAC inhibitors" relates to compounds which inhibit the histone deacetylase and which possess antiproliferative activity. This includes compounds disclosed in WO 02/22577, especially N-hydroxy-3-[4-[[(2-hydroxyethyl)[2-(1H-indol-3-yl)ethyl]-amino]methyl]phenyl]-2E-2-propenamide, N-hydroxy-3-[4-[[[2-(2-methyl-1H-indol-3-yl)-ethyl]-amino] methyl]phenyl]-2E-2-propenamide and pharmaceutically acceptable salts thereof. It further especially includes Suberoylanilide hydroxamic acid (SAHA).

The term "antineoplastic antimetabolite" includes, but is not limited to, 5-fluorouracil (5-FU); capecitabine; gemcitabine; DNA de-methylating agents, such as 5-azacytidine and decitabine; methotrexate; edatrexate; and folic acid antagonists such as pemetrexed. Capecitabine can be administered, e.g., in the form as it is marketed, e.g. under the trademark XELODA. Gemcitabine can be administered, e.g., in the form as it is marketed, e.g. under the trademark GEMZAR. Also included is the monoclonal antibody trastuzumab which can be administered, e.g., in the form as it is marketed, e.g. under the trademark HERCEPTIN.

The term "platin compound" as used herein includes, but is not limited to, carboplatin, cis-platin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity and further anti-angiogenic compounds" as used herein includes, but is not limited to: protein tyrosine kinase and/or serine and/or threonine kinase inhibitors or lipid kinase inhibitors, e.g.:

a) compounds targeting, decreasing or inhibiting the activity of the fibroblast growth factor-receptors (FGF-Rs);
b) compounds targeting, decreasing or inhibiting the activity of the insulin-like growth factor I receptor (IGF-IR), especially compounds which inhibit the IGF-IR, such as those compounds disclosed in WO 02/092599;
c) compounds targeting, decreasing or inhibiting the activity of the Trk receptor tyrosine kinase family;
d) compounds targeting, decreasing or inhibiting the activity of the Axl receptor tyrosine kinase family;
e) compounds targeting, decreasing or inhibiting the activity of the c-Met receptor;
f) compounds targeting, decreasing or inhibiting the activity of members of the protein kinase C (PKC) and Raf family of serine/threonine kinases, members of the MEK, SRC, JAK, FAK, PDK and Ras/MAPK family members, or PI(3) kinase family, or of the PI(3)-kinase-related kinase family, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; PD184352 or QAN697 (a P13K inhibitor);
g) compounds targeting, decreasing or inhibiting the activity of a protein-tyrosine kinase, such as imatinib mesylate (GLIVEC/GLEEVEC) or tyrphostin. A tyrphostin is preferably a low molecular weight (Mr<1500) compound, or a pharmaceutically acceptable salt thereof, especially a compound selected from the benzylidenemalonitrile class or the 5-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); and
h) compounds targeting, decreasing or inhibiting the activity of the epidermal growth factor family of receptor tyrosine kinases (EGF-R, ErbB2, ErbB3, ErbB4 as homo- or heterodimers), such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (HERCEPTIN), cetuximab, Iressa, erlotinib (Tarceva™), CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives which are disclosed in WO 03/013541.

Further anti-angiogenic compounds include compounds having another mechanism for their activity, e.g. unrelated to protein or lipid kinase inhibition e.g. thalidomide (THALOMID) and TNP-470.

Compounds which target, decrease or inhibit the activity of a protein or lipid phosphatase are e.g. inhibitors of phosphatase 1, phosphatase 2A, PTEN or CDC25, e.g. okadaic acid or a derivative thereof.

Compounds which induce cell differentiation processes are e.g. retinoic acid, α- γ- or δ-tocopherol or α- γ- or δ-tocotrienol.

The term "cyclooxygenase inhibitor" as used herein includes, but is not limited to, e.g. Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "bisphosphonates" as used herein includes, but is not limited to, etidronic, clodronic, tiludronic, pamidronic, alendronic, ibandronic, risedronic and zoledronic acid. "Etidronic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIA™. "Alendronic acid" can be administered, e.g., in the form as it is marketed, e.g. under the trademark FOSAMAX. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA.

The term "heparanase inhibitor" as used herein refers to compounds which target, decrease or inhibit heparin sulphate degradation. The term includes, but is not limited to, PI-88.

The term "biological response modifier" as used herein refers to a lymphokine or interferons, e.g. interferon γ.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor", e.g. L-744832, DK8G557 or R115777 (Zarnestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. PS-341 and MLN 341.

The term "matrix metalloproteinase inhibitor" or ("MMP inhibitor") as used herein includes, but is not limited to collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "agents used in the treatment of hematologic malignancies" as used herein includes, but is not limited to FMS-like tyrosine kinase inhibitors e.g. compounds targeting, decreasing or inhibiting the activity of Flt-3; interferon, 1-b-D-arabinofuransylcytosine (ara-c) and bisulfan; and ALK inhibitors e.g. compounds which target, decrease or inhibit anaplastic lymphoma kinase.

The term "compounds which target, decrease or inhibit the activity of Flt-3" are especially compounds, proteins or antibodies which inhibit Flt-3, e.g. PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; de-grading, targeting, decreasing or inhibiting the HSP90 client proteins via the ubiquitin proteasome pathway. Compounds targeting, decreasing or inhibiting the intrinsic ATPase activity of HSP90 are especially compounds, proteins or antibodies which inhibit the ATPase activity of HSP90 e.g., 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to trastuzumab (Herceptin™), Trastuzumab-DM1, ranibizumab (Lucentis®), bevacizumab (Avastin™), rituximab (Rituxan®), PRO64553 (anti-CD40) and 2C4 Antibody, and Eylea®. By antibodies is meant e.g. intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the first through seventieth embodiments can be used in combination with standard leukemia therapies, especially in combination with therapies used for the treatment of AML. In particular, compounds of the first through seventieth embodiments can be administered in combination with e.g. farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The structure of the active agents identified by code nos., generic or trade names may be taken from the actual edition of the standard compendium "The Merck Index" or from databases, e.g. Patents International (e.g. IMS World Publications).

The above-mentioned compounds, which can be used in combination with a compound of the first through seventieth embodiments, can be prepared and administered as described in the art such as in the documents cited above.

A compound of the first through seventieth embodiments may also be used to advantage in combination with known therapeutic processes, e.g., the administration of hormones or especially radiation.

A compound of first through seventieth embodiments may in particular be used as a radiosensitizer, especially for the treatment of tumors which exhibit poor sensitivity to radiotherapy.

In one embodiment, the invention provides a product comprising a compound of the first through seventieth embodiments and at least one other therapeutic agent as a combined preparation for simultaneous, separate or sequential use in therapy. In one embodiment, the therapy is the treatment of a disease or condition mediated by VEGF or a VEGF receptor activity. Products provided as a combined preparation include a composition comprising the compound of the first through seventieth embodiments and the other therapeutic agent(s) together in the same pharmaceutical composition, or the compound of the first through seventieth embodiments and the other therapeutic agent(s) in separate form, e.g. in the form of a kit.

In one embodiment, the invention provides a pharmaceutical composition comprising a compound of the first through seventieth embodiments and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of the first through seventieth embodiments. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of the first through seventieth embodiments in the manufacture of a medicament for treating a disease or condition mediated by VEGF or a VEGF receptor activity, wherein the medicament is prepared for administration with another therapeutic agent. The invention also provides the use of a another therapeutic agent in the manufacture of medicament for treating a disease or condition mediated by VEGF or a VEGF receptor activity, wherein the medicament is prepared for administration with a compound of the first through seventieth embodiments.

The invention also provides a compound of the first through seventieth embodiments for use in a method of treating a disease or condition mediated by VEGF or a VEGF receptor activity, wherein the compound of the first through seventieth embodiments is prepared for administration with another therapeutic agent. The invention also provides another therapeutic agent for use in a method of treating a disease or condition mediated by VEGF or a VEGF receptor activity, wherein the other therapeutic agent is prepared for administration with a compound of the first through seventieth embodiments. The invention also provides a compound of the first through seventieth embodiments for use in a method of treating a disease or condition mediated by VEGF or a VEGF receptor activity, wherein the compound of the first through seventieth embodiments is administered with another therapeutic agent. The invention also provides another therapeutic agent for use in a method of treating a disease or condition mediated by VEGF or a VEGF receptor activity, wherein the other therapeutic agent is administered with a compound of the first through seventieth embodiments.

The invention also provides the use of a compound of the first through seventieth embodiments in the manufacture of a medicament for treating a disease or condition mediated by VEGF or a A a VEGF receptor, wherein the patient has previously (e.g. within 24 hours) been treated with another therapeutic agent. The invention also provides the use of another therapeutic agent in the manufacture of a medicament for treating a disease or condition mediated by VEGF or the receptor thereof, wherein the patient has previously (e.g. within 24 hours) been treated with a compound of the first through seventieth embodiments.

The following examples are intended to illustrate the invention and are not to be construed as being limitations thereon. Temperatures are given in degrees centrigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

Based on the property of the compounds of the first through seventieth embodiments as potent VEGF receptor inhibitors, the compounds of the first through seventieth embodiments are especially suitable for the treatment of diseases associated with deregulated angiogenesis, especially diseases caused by ocular neovascularisation, especially retinopathies such as diabetic retinopathy or age-related macula degeneration, psoriasis, Von Hippel Lindau disease, hemangioblastoma, angioma, mesangial cell proliferative disorders such as chronic or acute renal diseases, e.g. diabetic nephropathy, malignant nephrosclerosis, thrombotic microangiopathy syndromes or transplant rejection, or especially inflammatory renal disease, such as glomerulonephritis, especially mesangioproliferative glomerulonephritis, haemolytic-uraemic syndrome, diabetic nephropathy, hypertensive nephrosclerosis, atheroma, arterial restenosis, autoimmune diseases, acute inflammation, including rheumatoid arthritis, fibrotic disorders (e.g. hepatic cirrhosis), diabetes, endometriosis, chronic asthma, arterial or post-transplantational atherosclerosis, neurodegenerative disorders, e.g. multiple sclerosis, and especially neoplastic diseases such as cancer (especially solid tumours but also leukemias), such as especially breast cancer, adenocarcinoma, colorectal cancer, lung cancer (especially non-small-cell lung cancer), renal cancer, liver cancer, pancreatic cancer, ovarian cancer or cancer of the prostate as well as myeloma, especially multiple myeloma, myelodysplastic syndrome, AML (acute myeloid leukemia), AMM (agnogenic myeloid metaplasia), mesothelioma, glioma and glioblastoma. A compound of the first through seventieth embodiments is especially suited also to preventing the metastatic spread of tumours and the growth of micrometastases. The compounds of the first through seventieth embodiments, due to their activity as kinases, are also useful as in treatment in connection with transplantation.

Crystalline Compounds

As used herein "polymorph" refers to crystalline forms having the same chemical composition but different spatial arrangements of the molecules, atoms, and/or ions forming the crystal.

As used herein "solvate" refers to a crystalline form of a molecule, atom, and/or ions that further comprises molecules of a solvent or solvents incorporated into the crystalline lattice structure. The solvent molecules in the solvate may be present in a regular arrangement and/or a non-ordered arrangement. The solvate may comprise either a stoichiometric or nonstoichiometric amount of the solvent molecules. For example, a solvate with a nonstoichiometric amount of solvent molecules may result from partial loss of solvent from the solvate. Solvates may occur as dimers or oligomers comprising more than one molecule or N-(1-methyl-5-(trifluoromethyl)-1H-pyrazol-3-yl)-5-((6-((methylamino)methyl)pyrimidin-4-yl)oxy)-1H-indole-1-carboxamide within the crystalline lattice structure.

As used herein "amorphous" refers to a solid form of a molecule, atom, and/or ions that is not crystalline. An amorphous solid does not display a definitive X-ray diffraction pattern.

As used herein, "substantially pure," when used in reference to a form, means a compound having a purity greater than 90 weight %, including greater than 90, 91, 92, 93, 94, 95, 96, 97, 98, and 99 weight %, and also including equal to about 100 weight % of N-(1-methyl-5-(trifluoromethyl)-1H-pyrazol-3-yl)-5-((6-((methylamino)methyl)pyrimidin-4-yl)oxy)-1H-indole-1-carboxamide, based on the weight of the compound. The remaining material comprises other form(s) of the compound, and/or reaction impurities and/or processing impurities arising from its preparation. For example, a crystalline form of N-(1-methyl-5-(trifluoromethyl)-1H-pyrazol-3-yl)-5-((6-((methylamino)methyl)pyrimidin-4-yl)oxy)-1H-indole-1-carboxamide may be deemed substantially pure in that it has a purity greater than 90 weight %, as measured by means that are at this time known and generally accepted in the art, where the remaining less than 10 weight % of material comprises other form(s) of N-(1-methyl-5-(trifluoromethyl)-1H-pyrazol-3-yl)-5-((6-((methylamino)methyl)pyrimidin-4-yl)oxy)-1H-indole-1-carboxamide and/or reaction impurities and/or processing impurities.

Another way to define substantially pure is following:

As used herein, the term "substantially pure" with reference to a particular polymorphic form means that the polymorphic form includes less than 10%, preferably less than 5%, more preferably less than 3%, most preferably less than 1% by weight of any other physical forms of the compound.

In one embodiment of the disclosure, a crystalline form of the N-(1-methyl-5-(trifluoromethyl)-1H-pyrazol-3-yl)-5-((6-((methylamino)methyl)pyrimidin-4-yl)oxy)-1H-indole-1-carboxamide is provided in substantially pure form. This crystalline form of N-(1-methyl-5-(trifluoromethyl)-1H-pyrazol-3-yl)-5-((6-((methylamino)methyl)pyrimidin-4-yl)oxy)-1H-indole-1-carboxamide in substantially pure form may be employed in pharmaceutical compositions which may optionally include one or more other components selected, for example, from the group consisting of excipients, carriers, and one of other active pharmaceutical ingredients active chemical entities of different molecular structure.

Preferably, the crystalline form has substantially pure phase homogeneity as indicated by less than 10%, preferably less than 5%, and more preferably less than 2% of the total peak area in the experimentally measured XRPD pattern arising from the extra peaks that are absent from the simulated PXRD pattern. Most preferred is a crystalline form having substantially pure phase homogeneity with less than 1% of the total peak area in the experimentally measured PXRD pattern arising from the extra peaks that are absent from the simulated PXRD pattern.

The term "essentially the same" with reference to X-ray diffraction peak positions means that typical peak position and intensity variability are taken into account. For example, one skilled in the art will appreciate that the peak positions (2θ) will show some inter-apparatus variability, typically as much as 0.2°. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measure only.

Preparation of Crystalline Materials:

Crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. High throughput crystallization techniques may be employed to prepare crystalline forms including polymorphs.

Crystals of drugs, including polymorphs, methods of preparation, and characterization of drug crystals are discussed in Solid-State Chemistry of Drugs, S. R. Byrn, R. R. Pfeiffer, and J. G. Stowell, $2^{nd}$ Edition, SSCI, West Lafayette, Ind. (1999).

For crystallization techniques that employ solvent, the choice of solvent or solvents is typically dependent upon one or more factors, such as solubility of the compound, crystallization technique, and vapor pressure of the solvent. Combinations of solvents may be employed, for example, the compound may be solubilized into a first solvent to afford a solution, followed by the addition of an antisolvent to decrease the solubility of the compound in the solution and to afford the formation of crystals. An antisolvent is a solvent in which the compound has low solubility.

In one method to prepare crystals, a compound is suspended and/or stirred in a suitable solvent to afford a slurry, which may be heated to promote dissolution. The term "slurry", as used herein, means a saturated solution of the compound, which may also contain an additional amount of the compound to afford a heterogeneous mixture of the compound and a solvent at a given temperature.

Seed crystals may be added to any crystallization mixture to promote crystallization. Seeding may be employed to control growth of a particular polymorph or to control the particle size distribution of the crystalline product. Accordingly, calculation of the amount of seeds needed depends on the size of the seed available and the desired size of an average product particle as described, for example, in "Programmed Cooling of Batch Crystallizers," J. W. Mullin and J. Nyvlt, *Chemical Engineering Science,* 1971, 26, 369-377. In general, seeds of small size are needed to control effectively the growth of crystals in the batch. Seed of small size may be generated by sieving, milling, or micronizing of large crystals, or by micro-crystallization of solutions. Care should be taken that milling or micronizing of crystals does not result in any change in crystallinity form the desired crystal form (i.e., change to amorphous or to another polymorph).

A cooled crystallization mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as solid state nuclear magnetic resonance, differential scanning calorimetry, x-ray powder diffraction, or the like, to assure formation of the preferred crystalline form of the product. The resulting crystalline form is typically produced in an amount of greater than about 70 weight % isolated yield, preferably greater than 90 weight % isolated yield, based on the weight of the compound originally employed in the crystallization procedure. The product may be co-milled or passed through a mesh screen to delump the product, if necessary.

Crystalline forms may be prepared directly from the reaction medium of the final process for preparing N-(1-methyl-5-(trifluoromethyl)-1H-pyrazol-3-yl)-5-((6-((methylamino)methyl)pyrimidin-4-yl)oxy)-1H-indole-1-carboxamide. This may be achieved, for example, by employing in the final process step a solvent or a mixture of solvents from which N-(1-methyl-5-(trifluoromethyl)-1H-pyrazol-3-yl)-5-((6-((methylamino)methyl)pyrimidin-4-yl)oxy)-1H-indole-1-carboxamide may be crystallized. Alternatively, crystalline forms may be obtained by distillation or solvent addition techniques. Suitable solvents for this purpose include, for example, the aforementioned nonpolar solvents and polar solvents, including protic polar solvents such as alcohols, and aprotic polar solvents such as ketones.

The presence of more than one polymorph in a sample may be determined by techniques such as x-ray powder diffraction (PXRD) or solid state nuclear magnetic resonance spectroscopy. For example, the presence of extra peaks in the comparison of an experimentally measured PXRD pattern with a simulated PXRD pattern may indicate more than one polymorph in the sample. The simulated PXRD may be calculated from single crystal x-ray data, see Smith, D. K., "*A FORTRAN Program for Calculating X-Ray Powder Diffraction Patterns,*" Lawrence Radiation Laboratory, Livermore, Calif., UCRL-7196 (April 1963) or TOPAS program (Total Pattern Analysis Solution, available through Brucker AXS Inc.).

Various Analytical Methods May be Used for Characterization.

I. X-Ray Powder Diffraction Measurements

One of ordinary skill in the art will appreciate that an X-ray diffraction pattern may be obtained with a measurement error that is dependent upon the measurement conditions employed. In particular, it is generally known that intensities in a X-ray diffraction pattern may fluctuate depending upon measurement conditions employed. It should be further understood that relative intensities may also vary depending upon experimental conditions and, accordingly, the exact order of intensity should not be taken into account. Additionally, a measurement error of diffraction angle for a conventional X-ray diffraction pattern is typically about 5% or less, and such degree of measurement error should be taken into account as pertaining to the aforementioned diffraction angles. Consequently, it is to be understood that the crystal forms of the instant invention are not limited to the crystal forms that provide X-ray diffraction patterns completely identical to the X-ray diffraction patterns depicted in the accompanying Figures disclosed herein. Any crystal forms that provide X-ray diffraction patterns substantially identical to those disclosed in the accompanying Figures fall within the scope of the present invention. The ability to ascertain substantial identities of X-ray diffraction patterns is within the purview of one of ordinary skill in the art.

II. Differential Scanning Calorimetry (DSC)

The DSC instrument used to test the crystalline forms was a TA Instrument® Differential Scanning calorimetry Model 2910, TA Instruments® Modulated Differential Scanning calorimetry Model 2920, or TA Instruments® Modulated Differential Scanning calorimetry Model Q1000. The DSC cell/sample chamber was purged with 100 ml/min of ultra-high purity nitrogen gas. The instrument was calibrated with high purity indium. The accuracy of the measured sample temperature with this method is within about ±1° C., and the heat of fusion can be measured within a relative error of about ±5%. The sample was placed into an open aluminum DSC pan and measured against an empty reference pan. About 2-6 mg of sample powder was placed into the bottom of the pan and lightly tapped down to make contact with the pan. The weight of the sample was measured accurately and recorded to a hundredth of a milligram. The instrument was programmed to heat at 10° C. per minute in the temperature range between 25 and 300° C.

The heat flow, which was normalized by a sample weight, was plotted versus the measured sample temperature. The data were reported in units of watts/gram ("W/g"). The plot was made with the endothermic peaks pointing down. The endothermic melt peak was evaluated for extrapolated onset temperature, peak temperature, and heat of fusion in this analysis.

III. Thermogravimetric Analysis (TGA)

The TGA instruments used to test the crystalline forms was a TA Instruments®. High Resolution Thermogravimetric Analyzer Q500 or TA Instruments®. High Resolution Thermogravimetric Analyzer 2950. Samples of 15 to 20 milligrams were analyzed at a heating rate of 10° C. per minute in the temperature range between 25° C. and about 300° C.

EXAMPLES

The invention is illustrated, but in no way limited, by the following Examples.
Abbreviations
ACN acetonitrile
app apparent
aq aqueous
atm atmosphere
ATP adenosine 5'-triphosphate
BOC tertiary butyl carboxy
BOP (benzotriazol-1-yloxy)tris(dimethylamino)phosphonium hexafluorophosphate
br broad
BSA bovine serum albumin
d doublet
DBU 1,8-diazabicyclo[5.4.0]undec-7-ene
DCE 1,2-dichloroethane
dd doublet of doublets
DCM dichloromethane
DIEA diisopropylethylamine
DMAP 4,4-dimethylaminopyridine
DME 1,4-dimethoxyethane
DMF N,N-dimethylformamide
DMP Dess-Martin reagent; 1,1,1-Triacetoxy-1,1-dihydro-1,2-benziodoxol-3(1H)-one
DMSO dimethylsulfoxide
DTT dithiothreitol
EDTA ethylenediaminetetraacetic acid
ESI electrospray ionization
EtOAc ethyl acetate
FCC flash column chromatography
g grams
g (italic) gravitational acceleration constant
GSH glutathione
h hour(s)
HATU 2-(1H-7-azabenzotriazol-1-yl)-1,1,3,3-tetramethyl uronium hexafluorophosphate methanaminium
HBTU 1-[bis(dimethylamino)methylene]-1H-benzotriazolium hexafluorophosphate(1-) 3-oxide
HOBt 1-hydroxy-7-azabenzotriazole
HPLC high performance liquid chromatography
IR infrared spectroscopy
LCMS liquid chromatography coupled to mass spectrometry
LTMP lithium 2,2',6,6'-tetramethylpiperidine
M molar
m multiplet
MeOH methanol
min minutes
mL milliliter(s)
mmol millimoles
MS mass spectrometry
MsOH methanesulfonic acid
m/z mass to charge ratio
N normal
NADPH beta-nicotinamide dinucleotide phosphate, reduced form
NMR nuclear magnetic resonance
Pd/C palladium on carbon
ppm parts per million
PyBOP benzotriazol-1-yloxytripyrrolidinophosphonium hexafluorophosphate
rac racemic
rt room temperature
$R_t$ retention time
s singlet
sat saturated
SFC Supercritical Fluid Chromatography
t triplet
TBSCl tert-butyldimethylsilyl chloride
TFA trifluoroacetic acid
THF tetrahydrofuran
UDPGA Uridine 5'-diphsopho-alpha-D-glucuronic acid Example 1—Preparation of (Z)—N-((6-((1-((1-methyl-5-(trifluoromethyl)-1H-pyrazol-3-yl)carbamoyl)-1H-indol-5-yl)oxy)pyrimidin-4-yl)methylene)methanamine oxide

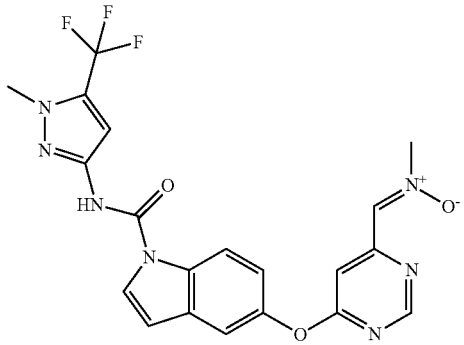 [SMILES: Cn1nc(NC(=O)n2ccc3cc(Oc4cc(/C=[N+](/C)[O-])ncn4)ccc32)cc1C(F)(F)F]

To a suspension of N-(1-methyl-5-(trifluoromethyl)-1H-pyrazol-3-yl)-5-((6-((methylamino)methyl)pyrimidin-4-yl)oxy)-1H-indole-1-carboxamide (3.06 g, 6.87 mmol), prepared as described in WO2010066684, in acetonitrile (140 mL) at room temperature was added a 30 wt % solution of H$_2$O$_2$ in water (147 mL, 1443 mmol). The reaction was allowed to stir for three hours. The mixture was then diluted with 500 mL of DCM followed by 400 mL water and the resulting layers were separated. The aqueous layer was extracted with an additional 250 mL of DCM. The organic layers were combined and then washed successively with brine (150 mL), then saturated NaHSO$_3$ (150 mL) and then once more with brine (150 mL). The organic phase was then dried over granular Na$_2$SO$_4$ filtered and concentrated. The resulting residue was partially purified by silica gel flash column chromatography (0 to 10% MeOH in DCM), and then further purified by precipitation from a warm (~60° C.) ethyl acetate solution by the slow addition of heptanes followed by slow cooling to room temperature. The resulting solid is collected by filtration and washed with cold 2:1 heptane:ethyl acetate to afford (Z)—N-((6-((1-((1-methyl-5-(trifluoromethyl)-1H-pyrazol-3-yl)carbamoyl)-1H-indol-5-yl)oxy)pyrimidin-4-yl)methylene)methanamine oxide in 25% yield. 1H NMR (400 MHz, DMSO-d6) δ=11.07 (s, 1H), 8.78 (d, J=1.0 Hz, 1H), 8.42 (d, J=1.5 Hz, 1H), 8.32 (d, J=9.1 Hz, 1H), 8.19 (d, J=3.5 Hz, 1H), 8.07 (s, 1H), 7.49 (d, J=2.5 Hz, 1H), 7.16 (dd, J=2.3, 8.8 Hz, 2H), 7.08 (s, 1H), 6.77 (d, J=4.0 Hz, 2H), 3.95 (s, 3H), 3.89 (s, 3H). HRMS: C$_{20}$H$_{17}$F$_3$N$_7$O$_3$ calculated 460.1345. found 460.1341.

Example 2—Preparation of 5-((6-Carbamoylpyrimidin-4-yl)oxy)-N-(1-methyl-5-(trifluoromethyl)-1H-pyrazol-3-yl)-1H-indole-1-carboxamide

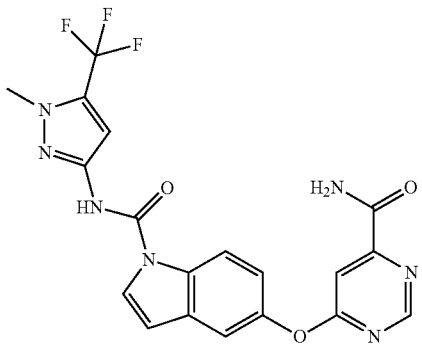 [SMILES: Cn1nc(NC(=O)n2ccc3cc(Oc4cc(C(N)=O)ncn4)ccc32)cc1C(F)(F)F]

To a solution of 5-((6-(hydroxymethyl)pyrimidin-4-yl)oxy)-N-(1-methyl-5-(trifluoromethyl)-1H-pyrazol-3-yl)-1H-indole-1-carboxamide (700 mg, 1.619 mmol) in DCM (20 ml), Dess-Martin Periodinane (1030 mg, 2.429 mmol) was added. The reaction was stirred for 2 h. At this point, an aqueous saturated solution of NaHCO$_3$ was added. The layers were separated and the organics extracted with DCM. The organic layers were combined dried over sodium sulfate and evaporated. To the resulting residue was added tBuOH (16 ml)/H$_2$O (4 ml), followed by sodium chlorite (946 mg, 8.37 mmol), sodium dihydrogen phosphate (1004 mg, 8.37 mmol) and 2-methyl-2-butene (6.65 ml, 62.7 mmol). The reaction stirred for 4 h. At this point a pH 7.4 phosphate buffer solution was added and the product extracted with EtOAc. To a portion of the crude mixture (100 mg, 0.224 mmol) in DCM (2 ml) at 0° C., oxalyl chloride (0.029 ml, 0.336 mmol) and DMF (1.735 µl, 0.022 mmol) were added. After 2 minutes 0.5 M ammonia in dioxane (13.44 ml, 6.72 mmol) was added and the reaction warmed to rt and stirred overnight. The reaction was evaporated and purified directly using FCC eluting with heptane:EtOAc 100:0 to 0:100. $^1$H NMR (400 MHz, DMSO-d$_6$) δ ppm 11.07 (s, 1H) 8.87 (d, J=1.01 Hz, 1H) 8.34 (d, J=8.84 Hz, 1H) 8.28 (s, 1H) 8.20 (d, J=3.79 Hz, 1H) 7.97 (s, 1H) 7.53 (d, J=2.02 Hz, 1H) 7.41 (d, J=1.01 Hz, 1H) 7.19 (dd, J=9.09, 2.53 Hz, 1H) 7.08 (s, 1H) 6.78 (d, J=3.79 Hz, 1H) 3.95 (s, 3H). MS (ESI+) m/z 445.93 (M+H).

Example 3—Preparation of 5-(6-(aminomethyl)pyrimidin-4-yloxy)-N-(1-methyl-5-(trifluoromethyl)-1H-pyrazol-3-yl)-1H-indole-1-carboxamide a) 5-(6-(benzyloxymethyl)pyrimidin-4-yloxy)-N-(1-methyl-5-(trifluoromethyl)-1H-pyrazol-3-yl)-1H-indole-1-carboxamide

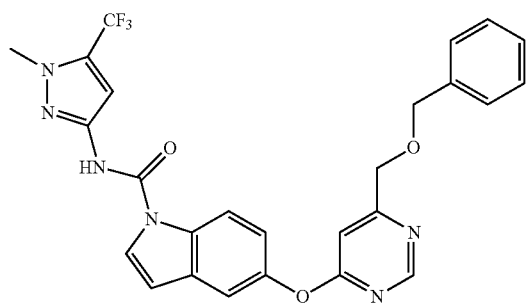 [SMILES: Cn1nc(NC(=O)n2ccc3cc(Oc4cc(COCc5ccccc5)ncn4)ccc32)cc1C(F)(F)F]

To a solution of 5-((6-((benzyloxy)methyl)pyrimidin-4-yl)oxy)-1H-indole (2.88 g, 8.69 mmol), prepared as described in WO010066684, and phenyl (1-methyl-5-(trifluoromethyl)-1H-pyrazol-3-yl)carbamate (3.10 g, 10.86 mmol), prepared as described in WO010066684, in DMF (87 ml) under nitrogen at 0° C. was added NaH (60% in mineral oil, 1.043 g, 26.1 mmol).

After 30 minutes the reaction was diluted with ethyl acetate (100 mL) and quenched with 30 mL of saturated aqueous NH$_4$Cl. Water (50 mL) was added. The aqueous layer was extracted with another 2×50 mL ethyl acetate. The combined organics were dried with magnesium sulfate, filtered, and concentrated. The crude oil was purified by flash column chromatography (0-100% Ethyl Acetate:Heptanes) to provide the title compound. MS (ESI+) m/z 523.0 (M+H).

b) 5-(6-(hydroxymethyl)pyrimidin-4-yloxy)-N-(1-methyl-5-(trifluoromethyl)-1H-pyrazol-3-yl)-1H-indole-1-carboxamide

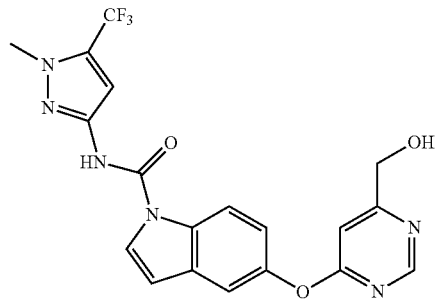 [SMILES: Cn1nc(NC(=O)n2ccc3cc(Oc4cc(CO)ncn4)ccc32)cc1C(F)(F)F]

5-(6-(benzyloxymethyl)pyrimidin-4-yloxy)-N-(1-methyl-5-(trifluoromethyl)-1H-pyrazol-3-yl)-1H-indole-1-carboxamide (3.26 g, 6.24 mmol) was taken up in TFA (100 ml) and heated at 100° C. After 3 hours the reaction was concentrated and purified by flash column chromatography (0-10% Methanol in DCM; Methanol contained 10% Ammonium Hydroxide) to provide the title compound. MS (ESI+) m/z 433.0 (M+H).

c) (6-(1-(1-methyl-5-(trifluoromethyl)-1H-pyrazol-3-ylcarbamoyl)-1H-indol-5-yloxy)pyrimidin-4-yl) methyl methanesulfonate

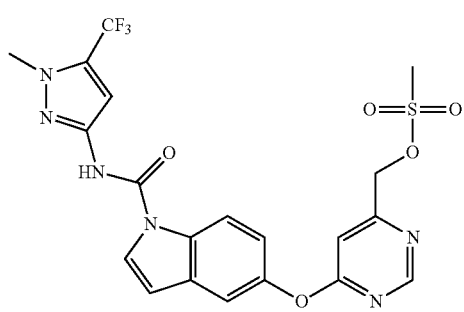 [SMILES: Cn1nc(NC(=O)n2ccc3cc(Oc4cc(COS(C)(=O)=O)ncn4)ccc32)cc1C(F)(F)F]

To a solution of 5-(6-(hydroxymethyl)pyrimidin-4-yloxy)-N-(1-methyl-5-(trifluoromethyl)-1H-pyrazol-3-yl)-1H-indole-1-carboxamide (0.93 g, 2.151 mmol) in DCM (19.55 ml) was added methanesulfonyl chloride (0.252 ml, 3.23 mmol), triethylamine (0.599 ml, 4.30 mmol) and DMAP (26 mg, 0.213 mmol). After 1 hour additional methanesulfonyl chloride (0.126 ml, 1.61 mmol) and triethylamine (0.300 ml, 2.15 mmol) were added. After 2 hours the reaction was quenched with water (20 ml) and extracted with DCM (3×10 ml), dried with MgSO$_4$, filtered and concentrated to give the title compound. MS (ESI+) m/z 510.9 (M+H).

d) 5-(6-(aminomethyl)pyrimidin-4-yloxy)-N-(1-methyl-5-(trifluoromethyl)-1H-pyrazol-3-yl)-1H-indole-1-carboxamide

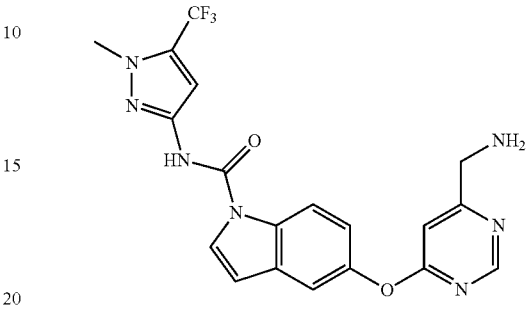

To a solution of (6-(1-(1-methyl-5-(trifluoromethyl)-1H-pyrazol-3-ylcarbamoyl)-1H-indol-5-yloxy)pyrimidin-4-yl) methyl methanesulfonate (107 mg, 0.210 mmol) in THF (2.10 ml) was added ammonia (0.5 M in Dioxane, 4.192 ml, 2.096 mmol). The reaction was stirred at room temperature for 1 day, then at 40° C. for 1 day. The reaction was concentrated and taken up in THF (2 ml) and ammonia (7 M in Methanol, 1.50 ml, 10.48 mmol) and heated at 35° C. overnight. The reaction was concentrated and absorbed onto silica to purify via FCC (0-5% Methanol in DCM; Methanol contained 10% Ammonium Hydroxide). The product was further purified by HPLC (20-100% acetonitrile:water gradient, Sunfire C8 OBD 5 um 30×100 column) to provide the title compound. $^1$H NMR (400 MHz, DMSO-d$_6$) δ ppm 8.65 (s, 1H) 8.32 (d, J=8.84 Hz, 1H) 8.18 (d, J=3.54 Hz, 1H) 7.46 (d, J=2.53 Hz, 1H) 7.10-7.15 (m, 2H) 7.07 (s, 1H) 6.76 (d, J=3.79 Hz, 1H) 3.95 (d, J=1.01 Hz, 3H) 3.82 (s, 2H). HRMS calcd. for C$_{19}$H$_{16}$F$_3$N$_7$O$_2$ (M+H)$^+$432.1396. found 432.1407.

Example 4—Isolation/characterization of other metabolites of N-(1-methyl-5-(trifluoromethyl)-1H-pyrazol-3-yl)-5-((6-(((methylamino)methyl)pyrimidin-4-yl)oxy)-1H-indole-1-carboxamide In-Vitro Protocol

[$^{14}$C]N-(1-methyl-5-(trifluoromethyl)-1H-pyrazol-3-yl)-5-(6-((methylamino)methyl)pyrimidin-4-yloxy)-1H-indole-1-carboxamide was incubated with hepatocytes from male Sprague-Dawley rats, male New Zealand White rabbits, male cynomolgus monkeys and humans (mixed males and females) at 10 μmol/L concentrations for 6 h. Incubations of 10 μmol/L [$^{14}$C]N-(1-methyl-5-(trifluoromethyl)-1H-pyrazol-3-yl)-5-(6-((methylamino)methyl)pyrimidin-4-yloxy)-1H-indole-1-carboxamide with human liver microsomes for 1 h were also performed. The incubates were analyzed by HPLC with radioactivity detection. Metabolite structures were characterized by LC-MS.

Summarized Metabolic Pathways of [$^{14}$C]N-(1-methyl-5-(trifluoromethyl)-1H-pyrazol-3-yl)-5-(6-((methylamino)methyl)pyrimidin-4-yloxy)-1H-indole-1-carboxamide in Hepatocytes and Human Liver Microsomes

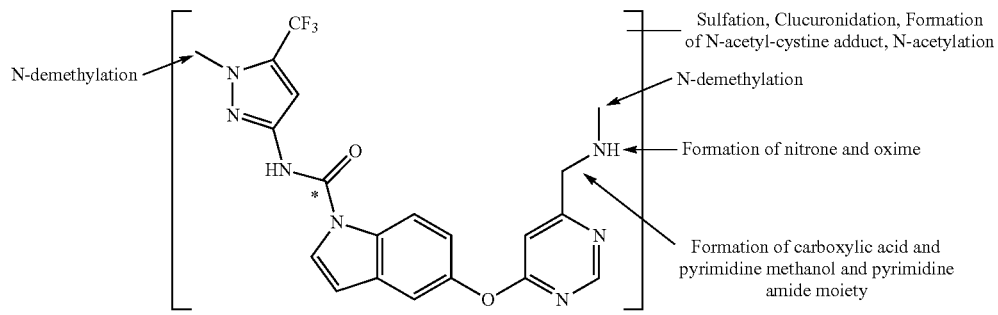

[$^{14}$C]N-(1-methyl-5-(trifluoromethyl)-1H-pyrazol-3-yl)-5-(6-((methylamino)methyl)pyrimidin-4-yloxy)-1H-indole-1-carboxamide and none-radioactively labeled N-(1-methyl-5-(trifluoromethyl)-1H-pyrazol-3-yl)-5-(6-((methylamino)methyl)pyrimidin-4-yloxy)-1H-indole-1-carboxamide were dissolved in DMSO to obtain solutions with a concentration of 10 mmol/L. In order to facilitate LC-MS analysis the degree of $^{14}$C-labeling in the final stock solution was adjusted to approx. 50%. Therefore 60 µL of the [$^{14}$C]N-(1-methyl-5-(trifluoromethyl)-1H-pyrazol-3-yl)-5-(6-((methylamino)methyl)pyrimidin-4-yloxy)-1H-indole-1-carboxamide solution was mixed with 40 µL of the non-radioactive N-(1-methyl-5-(trifluoromethyl)-1H-pyrazol-3-yl)-5-(6-((methylamino)methyl)pyrimidin-4-yloxy)-1H-indole-1-carboxamide solution. The cryopreserved hepatocytes described in Table 1 were used in this study.

TABLE 1

Origin of Used Hepatocytes

| | Species | | | |
|---|---|---|---|---|
| | Rat | Rabbit | Monkey | Human |
| Pooled/No. of donors | Pooled/n = 14 | Pooled/n = 3 | Pooled/n = 3 | Pooled/n = 20 |
| Strain | Sprague Dawley | New Zealand white rabbit | Cynomolgus | mixed |
| Gender | male | male | male | mixed |
| Supplier | Celsis | Celsis | Celsis | Celsis |
| Order number | M00005 | M00405 | M00305 | X008000 |
| Batch | LSC | BMC | OAY | SSY |

The cryopreserved hepatocytes were stored on liquid N2. On the day of the incubations, the hepatocytes were thawed according to the instructions provided by the supplier.

Hepatocyte Incubations and Viability Measurements

After thawing the cryopreserved hepatocytes, the viable cells were enriched by centrifugation in HepatoZYME cell culture medium (Gibco Invitrogen). For this purpose, the cells were added to 45 mL of a 37° C. warm HepatoZYME, and centrifuged at room temperature, at 50 g for 5 min. The supernatant containing dead cells was discarded and the cells in the pellet were re-suspended in HepatoZYME.

The viability of the re-suspended hepatocytes was determined by a Guava EasyCyte™ Mini system using the ViaCount® assay as described by the supplier (Guava Technologies, Hayward, Calif., USA). After cell counting, the cell concentration was adjusted to approx. $1 \cdot 10^6$ viable cells/mL by adding HepatoZYME. Subsequently, the incubations were started by adding [$^{14}$C]-(1-methyl-5-(trifluoromethyl)-1H-pyrazol-3-yl)-5-(6-((methylamino)methyl)pyrimidin-4-yloxy)-1H-indole-1-carboxamide and non-labeled N-(1-methyl-5-(trifluoromethyl)-1H-pyrazol-3-yl)-5-(6-((methylamino)methyl)pyrimidin-4-yloxy)-1H-indole-1-carboxamide as a solution in DMSO. The final concentration of DMSO in the incubations was 0.1% (v/v).

The initial concentration of [$^{14}$C]-(1-methyl-5-(trifluoromethyl)-1H-pyrazol-3-yl)-5-(6-((methylamino)methyl)pyrimidin-4-yloxy)-1H-indole-1-carboxamide in the incubates was 10 µmol/L (4.2 kBq/mL) for the metabolite pattern analyses. For all incubations, 25 mL tissue culture flasks (Becton Dickinson Franklin Lakes) were used and aliquots of 500 µL were taken at the different time points (0 h and 6 h).

To check the chemical stability of [$^{14}$C]N-(1-methyl-5-(trifluoromethyl)-1H-pyrazol-3-yl)-5-(6-((methylamino)methyl)pyrimidin-4-yloxy)-1H-indole-1-carboxamide under the incubation conditions, the compound was incubated at a concentration of 10 µmol/L in HepatoZYME without hepatocytes. A second series of control incubations was performed with hepatocytes of all species in the absence of the test compound to investigate the effect of the latter on the viability. These experiments were performed in a 12×6 mL MultiWell™ plate (Art. 393503, Beckton Dickinson). Further details of the incubations are given in Table 2.

TABLE 2

Hepatocyte Incubation Conditions for Metabolite Patterns and Characterization of Metabolite Structures

| | | Species | | | |
|---|---|---|---|---|---|
| | | Rat | Rabbit | Monkey | Human |
| Initial substrate concentration | µmol/L | 10 | 10 | 10 | 10 |
| RA concentration (measured at 6 h) | dpm/mL | $7.26 \times 10^5$ | $4.93 \times 10^5$ | $7.31 \times 10^6$ | $6.50 \times 10^6$ |

TABLE 2-continued

Hepatocyte Incubation Conditions for Metabolite Patterns and Characterization of Metabolite Structures

| | | Species | | | |
|---|---|---|---|---|---|
| | | Rat | Rabbit | Monkey | Human |
| Volume of substrate solution added (10 mmol/L in DMSO) | µL | 6.35 | 4.20 | 4.00 | 5.95 |
| Initial concentration of viable cells | $10^6$/mL | 1.00 | 1.00 | 1.00 | 1.00 |
| Viability at 0 h | % | 88 | 70 | 93 | 76 |
| Viability at 6 h | % | 22 | 8 | 42 | 25 |
| Incubation time | h | 6 | 6 | 6 | 6 |
| Incubation volume | mL | 6.35 | 4.20 | 4.00 | 5.95 |

The incubations were performed at 37° C. under a humidified atmosphere of 95% relative humidity and 5% $CO_2$ in a Heraeus incubator/cytoperm (Kendro Laboratory Products AG, Zürich, Switzerland). During the incubations, the plates and flasks were shaken at 300 strokes per minute. The viability of the hepatocytes was determined after 6 h (end of incubation).

Assessment of Metabolic Stability of Radioactive Label

Additional incubations of N-(1-methyl-5-(trifluoromethyl)-1H-pyrazol-3-yl)-5-(6-((methylamino)methyl)pyrimidin-4-yloxy)-1H-indole-1-carboxamide were performed separately in order to assess the metabolic stability of the radioactive label. The incubations were performed as described before, but for the monkey hepatocytes a new batch (SZH) was used. At the time points 0, 2, 4, and 6 hours 50 µL aliquots (quadruplicate samples) were pipetted directly into 20 mL Zinsser vials containing 10 mL Rialuma (Lumac, The Netherlands). Additional 50 µL aliquots (quadruplicate samples) were pipetted into empty 20 mL Zinsser vials, where the samples were dried over night, before they were mixed with 10 mL Rialuma and sonicated for 60 minutes for radioactivity measurements.

Human Liver Microsomes Incubation

In this study, the commercially available human liver microsomes described in Table 3 were used. The lot was characterized with regard to the activity of various enzymes by the supplier (data not shown but kept on file). The microsomes were received on dry ice and stored at −80° C. until use.

TABLE 3

Technical Data on Liver Microsomes

| Species | Human |
|---|---|
| Gender | pool of females and males |
| Supplier | Gentest |
| Catalog/product no. | 457081 |
| Lot no. | 82087 (Novartis Global batch) |
| Number of individuals pooled | 50 |
| Protein content (mg/mL) | 20 |

Microsomal Incubations for Metabolite Patterns

Microsomal incubations for metabolite profiles were performed at 10 µmol/L of [$^{14}$C]N-(1-methyl-5-(trifluoromethyl)-1H-pyrazol-3-yl)-5-(6-((methylamino)methyl)pyrimidin-4-yloxy)-1H-indole-1-carboxamide (approx. 50% radiolabeled) with one time point investigated (60 min). Incubations were performed at 37° C. in 0.1 mol/L sodium phosphate buffer pH 7.4. The final concentrations in the incubation cocktail were: 4 mmol/L UDPGA (Sigma-Aldrich), 1 mmol/L β-NADPH (Sigma-Aldrich), 5 mmol/L $MgCl_2$, and 60 µg alamethicin (Sigma-Aldrich) per mg microsomal protein. The system was left to incubate for 10 min before adding the test compound to allow the pore formation with the alamethicin. The metabolic reaction was started by the addition of [$^{14}$C]N-(1-methyl-5-(trifluoromethyl)-1H-pyrazol-3-yl)-5-(6-((methylamino)methyl)pyrimidin-4-yloxy)-1H-indole-1-carboxamide and terminated by addition of two volumes of ice-cold acetonitrile. Samples were stored at −20° C. until analysis. Control incubations in the absence of microsomes were performed to determine the chemical stability of [14C]N-(1-methyl-5-(trifluoromethyl)-1H-pyrazol-3-yl)-5-(6-((methylamino)methyl)pyrimidin-4-yloxy)-1H-indole-1-carboxamide in the incubation mixture over 60 min.

TABLE 4

Liver Microsomes Incubation Conditions for Metabolite Patterns and Characterixation of Metabolite Structures

| | units | Human liver microsomes |
|---|---|---|
| Initial substrate concentration | µmol/L | 10 |
| Radioactivity concentration | dpm/mL | $6.93 \times 10^5$ |
| Volume of substrate solution (10 mmol/L in DMSO) added per mL final incubate | µL | 1.0 |
| Incubation times | min | 60 |
| Incubation volume | mL | 1.0 |

Sample Preparation

Test Compound and Conditions

A 10 mmol/L stock solution of [$^{14}$C]N-(1-methyl-5-(trifluoromethyl)-1H-pyrazol-3-yl)-5-(6-((methylamino)methyl)pyrimidin-4-yloxy)-1H-indole-1-carboxamide in DMSO was used for microsomal and hepatocyte incubations.

Sampling Times

The metabolite profiles with all species were performed at 6 h incubation time with hepatocytes, whereas the metabolite profile with human liver microsomes was performed at 1 h incubation time.

Incubation Methods for Metabolite Profiles

For hepatocytes incubations, [$^{14}$C]N-(1-methyl-5-(trifluoromethyl)-1H-pyrazol-3-yl)-5-(6-((methylamino)methyl)pyrimidin-4-yloxy)-1H-indole-1-carboxamide was incubated at an initial concentration of 10 µmol/L in a serum-free culture medium (HepatoZYME) with approx. $1*10^6$ viable hepatocytes/mL.

For human liver microsomes incubations, [$^{14}$C]N-(1-methyl-5-(trifluoromethyl)-1H-pyrazol-3-yl)-5-(6-((methylamino)methyl)pyrimidin-4-yloxy)-1H-indole-1-carboxamide was incubated at an initial concentration of 10 μmol/L in phosphate buffer containing 0.5 mg microsomes/L with the cofactors NADPH, GSH and UDPGA.

Structural characterization of the metabolites was accomplished by online radioactivity detection and LC-MS analysis (including accurate mass measurements) using incubation supernatants from hepatocytes and microsomes.

Sample Preparation

At the end of the incubation period, 500 μL aliquots of the incubation suspensions were mixed with two volumes of ice-cold acetonitrile to stop the enzymatic reactions. The mixtures were vortex-mixed and then stored for at least four hours at −20° C. until analysis to complete the protein precipitation. Then, each sample was thawed and centrifuged at 10000 g for 10 min, followed by removal of the supernatant S1. The supernatant S1 was evaporated using a sample concentrator, and stored at −20° C. until further use. Prior to HPLC injection, the concentrated sample was diluted with mobile phase A.

The resulting pellet was solubilized with 500 μL Solvable/isopropanol 2/1 (v/v) and neutralized with 200 μL hydrochloric acid (2 M).

Radioactivity Measurements for Determination of Recoveries

Radioactivity was measured with a Liquid Scintillation Analyzer (model TriCarb 2200CA, Packard Inst.). Aliquots (50 μL) of the incubation mixtures were measured after addition of 10-15 mL scintillation cocktail (Rialuma). Solubilized pellets were measured after addition of 17.5 mL scintillation cocktail (IrgaSafe Plus, Zinsser analytic, Frankfurt, Germany).

For the calculation of the total recovery in the incubations, the pellets must be solubilized and it is possible, that some radioactivity is lost. However, the radioactivity recovery in the pellets and the reconstituted supernatants of the four species at 6 h ranged between 92.3% and 97.7%, and was thus assumed to be almost complete.

The radioactivity in the pellets of the hepatocyte incubations was found to be less than 1.1% in all samples at 0 h and less than 4.5% at 6 h. In the pellets of the human liver microsomal incubations, the radioactivity was 0.7% at 0 h and 1.3% at 1 h, the end of the incubation. The radioactivity in the pellets of the supplementary hepatocyte incubations ranged between 4.2% and 9.5% in all samples at 6 h.

Viability of Hepatocytes

During incubation with [$^{14}$C]N-(1-methyl-5-(trifluoromethyl)-1H-pyrazol-3-yl)-5-(6-((methylamino)methyl)pyrimidin-4-yloxy)-1H-indole-1-carboxamide (10 μmol/L), the viability of the hepatocytes (percent viable cells relative to total cells) from rat, rabbit, monkey, and human decreased from initially 70-93% to 8-42% after 6 hours. The rate of decrease in viability followed the order: (human≈monkey) <rat<rabbit. Control incubations in absence of the compound showed a somewhat lower viability of 4-21% after 6 hours.

Stock Solution and Control Incubation

The [$^{14}$C]N-(1-methyl-5-(trifluoromethyl)-1H-pyrazol-3-yl)-5-(6-((methylamino)methyl)pyrimidin-4-yloxy)-1H-indole-1-carboxamide stock solution used in the current study was analyzed by HPLC with online radioactivity detection. The radiochemical purity was 99.6%. The total sum of all impurities accounted for 0.4%. Control incubations of [$^{14}$C]N-(1-methyl-5-(trifluoromethyl)-1H-pyrazol-3-yl)-5-(6-((methylamino)methyl)pyrimidin-4-yloxy)-1H-indole-1-carboxamide in the absence of hepatocytes or liver microsomes confirmed the stability of the compound during the incubations in the incubation media.

In-Vivo Protocol

Animals

Animal License Numbers

No. 18, Kantonales Veterinäramt Basel

Species, Strain, Gender

Rat, Wistar (Han:WIST, albino), male Rat, Brown Norway (BN/Crl, pigmented), male Supplier Han:WIST: Harlan, The Netherlands BN/Crl: Janvier, France Water/Feeding free access to tap water and NAFAG pellets No. 890 (Eberle NAFAG AG, Gossau, Switzerland) throughout the study Environmental Conditions

22±2° C.

Formulations

The test formulation was freshly prepared on the day of administration. The drug substance was dissolved in 10% N-methyl pyrolidone (NMP), 70% mono-dispersed PEG200 (tetra-ethylene glycol), and 20% aqueous 0.9% NaCl solution. For 10 mg of compound, one gram of NMP was added up to dissolve the compound, then 7 g of PEG200 and 2 g of 0.9% NaCl were successively added to achieve a total of 10 g.

Dosing

The dosing solution (1 g/kg) was administered as a bolus into the *Vena femoralis* of all rats anesthetized by inhalation of an oxygen/isoflurane (Forene) mixture (97/3, v/v). The nominal dose was 1 mg/kg.

Blood/Plasma

Blood samples were collected sublingually. For sample collection, the rats were anesthetized by inhalation of an oxygen/isoflurane (Forene) mixture (97/3, v/v). The sublingual vein was punctured using a fine needle and the required blood was collected in K3-EDTA vials. The bleeding was stopped within 10 to 15 s by pressing a swab on the wound. The rats were unconscious for about 2 to 3 min per sample collection.

The collected blood was centrifuged within 10 min after collection (3000 g, 10 min, and room temperature). Plasma was separated, and an aliquot of 20 μL was removed, weighed, and assayed for radioactivity by LSC. The remaining plasma was stored at approximately −80° C. until determination of N-(1-methyl-5-(trifluoromethyl)-1H-pyrazol-3-yl)-5-(6-((methylamino)methyl)pyrimidin-4-yloxy)-1H-indole-1-carboxamide by ABA (Groups 1, 5a) or IDD (Groups 2). For blood sampled in Groups 3 and 4, a 20 μL aliquot of the collected blood was removed, weighed, and assayed for radioactivity by LSC.

Excreta, Carcass, and Cage Wash

Urine and feces were collected quantitatively from each rat of Groups 2, and 5a. Urine was collected on dry ice. Feces were collected at room temperature. After each urine collection, the collection vial was rinsed with 3 to 5 mL of water which was added to the respective urine sample. Two aliquots of each urine sample (each ~0.05 g) were removed, weighed, and processed for determination of radioactivity. Remaining urine was stored at approximately −80° C. until analysis by IDD. Each feces sample was weighed, and a 1% aqueous carboxymethyl cellulose solution (about 10 times the feces weight) was added, followed by homogenization using a rotating knife homogenizer (Polytron). Three aliquots of each feces homogenate (each 2 to 3 g) were removed, weighed, and processed for determination of radioactivity after trapping of CO2. Remaining feces homogenate was stored at approximately −20° C. until analysis by IDD.

The carcasses were collected in Groups 2 and 5a at the end of the study. These were further processed for determination of radioactivity. Cage wash was obtained by rinsing the cages with Radiacwash (Biodex Medical Systems, New York, USA; 1:10 diluted), water, and ethanol. All liquids used for the washing procedure were collected together for determination of radioactivity.

Volatile CO2 Trapping
In Vivo CO2 Trapping

The two rats 1a and 2a of Group 5a were maintained in adapted metabolism glass cages for 48 h. The radioactivity of the total 14CO2 captured was determined in the two trapping media ethanolamine:methanol (1:10) and methanol from each rat according to the sampling schedule.

CO2 Trapping from Feces

Vials containing feces homogenates were opened in a chamber maintained under airflow (2.1-3.6 mL/min). The flow was bubbling into two consecutive flasks containing trapping media ethanolamine:methanol (1:10) and methanol, respectively. Those media were processed for determination of radioactivity.

Liquid Scintillation Counting

The radioactivity in aliquots of biological samples (blood, plasma, urine, feces, and carcass) and other samples (dosing solutions, cage wash, trapping solutions) was measured by LSC using 2500 TR liquid scintillation counters from Packard Instr. For quench correction, an external standard method was used. Quench correction curves were established by means of sealed standards (Packard Instr.). Background values were obtained for each batch of samples using blank samples of the respective matrix. The LOD was defined as 1.8 times the background value. All determinations of radioactivity were performed using weighed samples.

Radioactivity Measurements During Sample Preparation

Radioactivity contents in biological samples and recoveries of radioactivity after sample preparation for metabolite patterns were determined by liquid scintillation counting as follows: Homogeneous samples (plasma, urine, feces, extracts) were measured directly in 20 mL antistatic polyethylene vials (Packard BioScience, Groningen, The Netherlands) containing 10-20 mL Irgasafe Plus liquid scintillation cocktail (Perkin Elmer). Inhomogeneous samples (feces, pellets) were solubilized in a mixture of 0.5-2 mL Solvable (Perkin-Elmer)/isopropanol (1:1, v/v). After complete dissolution, the samples were neutralized with hydrochloric acid and mixed with 15-20 mL of Rialuma liquid cintillation cocktail (Zinsser Analytic Maidenhead, Berkshire, UK) for liquid scintillation counting. The radioactivity in the feces pool 0-48 h was determined using the CO2 trapping method. The samples were assayed for 14C-radioactivity in a LSC counter model Tri-Carb (Packard Instruments, Meriden, Conn., USA) using an external standard ratio method for quench correction.

Sample Preparation Methods Plasma (for Metabolite Patterns)

For the metabolite pattern analyses, plasma pools (identical volumes, ranging from 3 to 15 μL per time point and rat) were prepared for the following time points after dosing: (0.083 h, 0.5 h, 1 h, 4 h, 8 h, and 24 h) (n=4/sampling). The plasma samples were directly used for HPLC analysis with radioactivity detection. Prior to injection onto HPLC, 20 μL of a mixture containing the reference compounds and 230 μL solvent A were added. The HPLC recovery of the radioactivity was measured in a separate representative run with a 0.5 h and 8 h plasma pool (n=4). The recovery ranged between 93.4 and 106.2%, respectively. Hence, recovery of the radioactivity was shown to be complete.

The HPLC recovery of the radioactivity was measured in a separate representative run with a 0.5 h and 8 h plasma pool (n=4). The recovery ranged between 93.4 and 106.2%, respectively. Hence, recovery of the radioactivity was shown to be complete. to a weighed aliquot of feces homogenate (11.72 g). The mixture was vortexed for 1 min and sonicated for 15 min, followed by centrifugation at 2000 g for 15 min. Then the supernatant S1 was removed from the pellet P1. In a second extraction step, the pellet P1 was dissolved in 10 mL water and extracted with 30 mL of acetonitrile as described before, yielding supernatant S2 and pellet P2. The supernatant S2 was removed and the pellet P2 was dissolved in 10 mL water and extracted a third time with 35 mL of methanol, yielding supernatant S3 and pellet P3. The total extraction yield in the supernatants S1 to S3 was 91.3%. The supernatants S1 to S3 were combined and an aliquot of the mixture was injected directly on the HPLC system followed by offline radiodetection. The HPLC recovery of the radioactivity, measured in a separate run (feces pool 0-48 h), was 100.3%, and was thus considered to be complete.

HPLC Method for Metabolite Profiling and Identification
LC Instrumentation

HPLC system model 1100 (Agilent Technologies), equipped with a binary capillary pump model G1376A, a degasser model G1379A and a UV/VIS diode array detector model G1315B with a standard 13 μL flow cell model G1315-60012. UV spectra were monitored in the range of 200-800 nm. The operating software for the HPLC system was Agilent ChemStation for LC 3D, Rev. B.04.02.

Guard Column

ACE 3 C18 Guard Cartridge, 15 mm×4.6 mm i.d., Art. ACE-111-0103GD (ACT, Aberdeen, Scotland).

Analytical Column

ACE 3 C18, 3 μm, 150 mm×4.6 mm i.d., Art. ACE-111-1546 (ACT)

Column Conditions

Thermostated at 40° C. in a column chiller model 7955 (Jones Chromatography Ltd., Hengoed, Mid. Glamorgan, U.K.)

Injection Volume

Volumes up to 250 μL were injected into a 500 μL sample loop using a HTS PAL autosampler (CTC, Zwingen, Switzerland).

HPLC Analysis with UV Detection

After the chromatography the effluent was split into a ratio of approximately 1:20. The smaller amount was directed into the electrospray LC-MS interface. The bigger part was used for UV detection followed by online radioactivity detection.

Online Radioactivity Detection

A HPLC radioactivity monitor model LB 513 equipped with a flow cell model Z-500-5 (Berthold Technologies) was used. Therefore the effluent was mixed with Rialuma liquid scintillation mixture (Perkin Elmer) at a flow rate of 3 mL/min. The chromatograms were evaluated using Radio-Star software (Berthold).

Mobile Phase

A: 10 mM ammonium formate plus 1 mL/L formic acid; pH=3.58

B: acetonitrile plus 1 mL/L formic acid

Flow Rate
    1000 μL/min
Gradient
    0-5 min: 10% B; 5-50 min: 10-60% B; 50-55 min: 60-100% B; 55-60 min: 100% B
MS Method for Metabolite Identification
MS Instrumentation
    Time-of-flight (Q-Tof Premier) mass spectrometer (Waters, Manchester, UK) operated under MassLynx, Version 4.1.
Cone Voltage
    30 V
Collision Energy
    For the fragmentation of the molecules in the collision cell, collision energies of 15-35 eV were applied.
Desolvation Gas
    Nitrogen
Ionization Mode
    Electrospray in positive ion mode, Z-spray interface with LockSpray™ option.
Accurate Mass Measurement
    The reference channel of the LockSpray interface was operated with a solution of leucine-enkephalin (200 pg/μL) in a mixture of acetonitrile/water/formic acid 50/50/0.1 (v/v/v) at a flow rate of 5 μL/min. During data acquisition from the reference channel, the cone voltage was set to 40 V and the collision energy was set to 5 eV.
Temperatures
    Source block: 100° C.; Desolvation: 200° C.
Interpretation of Mass Fragmentation of N-(1-methyl-5-(trifluoromethyl)-1H-pyrazol-3-yl)-5-(6-((methylamino)methyl)pyrimidin-4-yloxy)-1H-indole-1-carboxamide and Nomenclature of Fragment Ions
    The electrospray mass spectrum of [$^{14}$C]N-(1-methyl-5-(trifluoromethyl)-1H-pyrazol-3-yl)-5-(6-((methylamino)methyl)pyrimidin-4-yloxy)-1H-indole-1-carboxamide showed the protonated intact molecular ion M+H$^+$ (m/z 446), and the two major key fragment ions A (m/z 255) and B (m/z 212). To a minor extent N-(1-methyl-5-(trifluoromethyl)-1H-pyrazol-3-yl)-5-(6-((methylamino)methyl)pyrimidin-4-yloxy)-1H-indole-1-carboxamide fragmented at the ether bond, leading to fragment C (m/z 122). Other fragments were less useful for structural assignments. Due to the significant degree of labeling (approx. 50%), fragment ions containing the $^{14}$C-label could be observed in the mass spectra and were in agreement with the proposed structures.

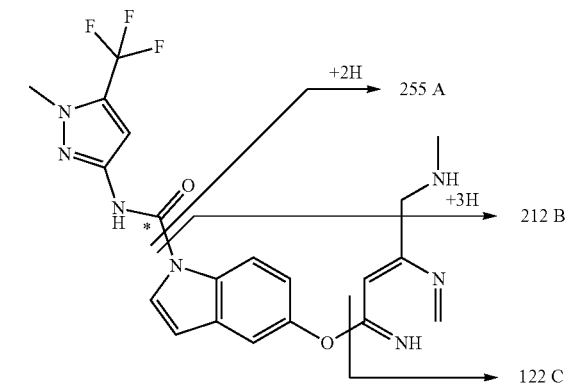

* position of $^{14}$C label

Proposed Structures of the Metabolites
    Metabolite structures were characterized by LC-MS using electrospray in positive ion mode. Mass spectral data, interpretation of the mass fragments and proposed structures are depicted below. Metabolite structures were supported by exact mass measurements and/or hydrogendeuterium exchange experiments. Increases in mass of the M+H$^+$ ions upon replacing the H$_2$O in the mobile phase by D$_2$O were in agreement with the proposed structures. This assignment of claimed metabolites was subsequently confirmed by comparison of retention time and mass spectral data with the available reference compounds.

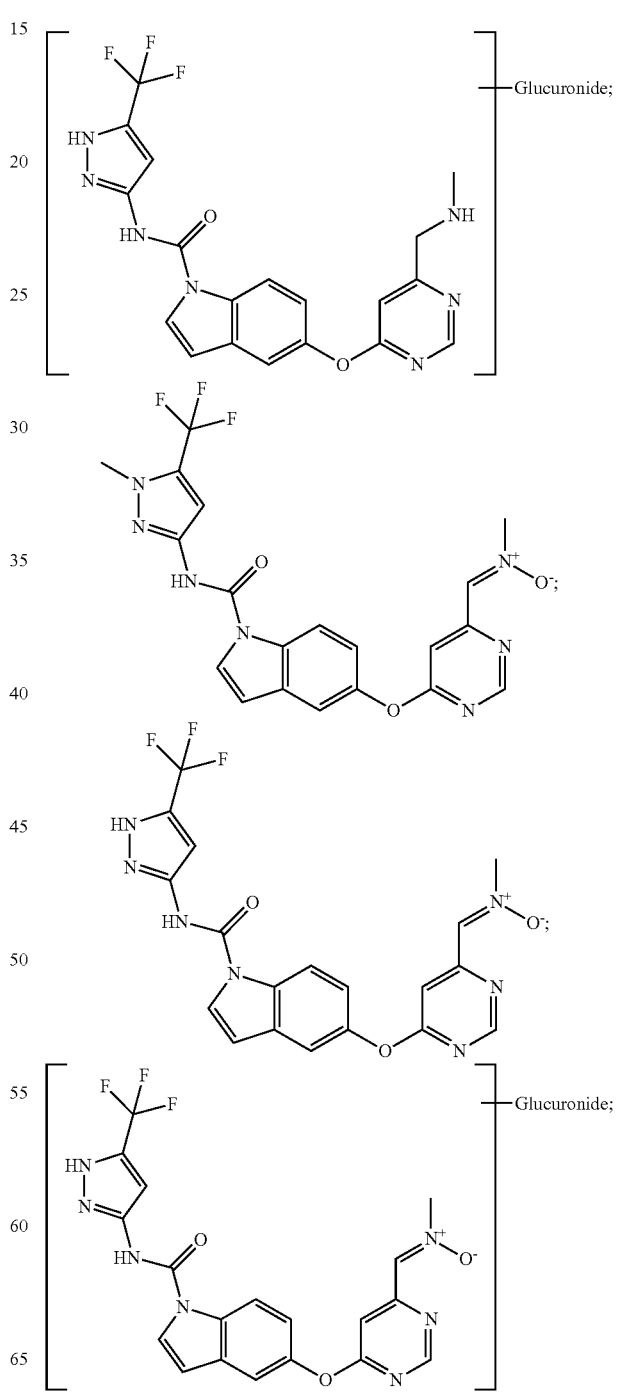

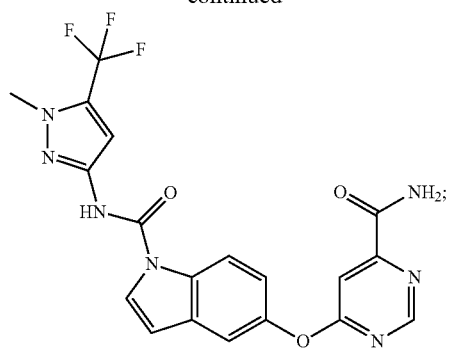

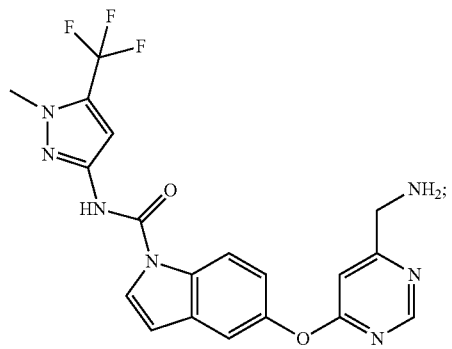

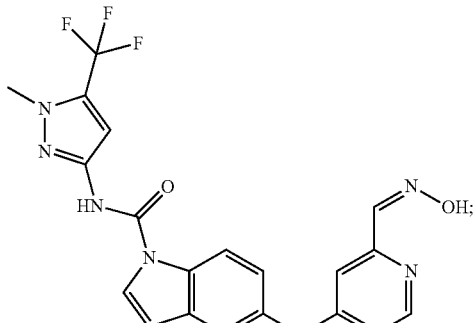

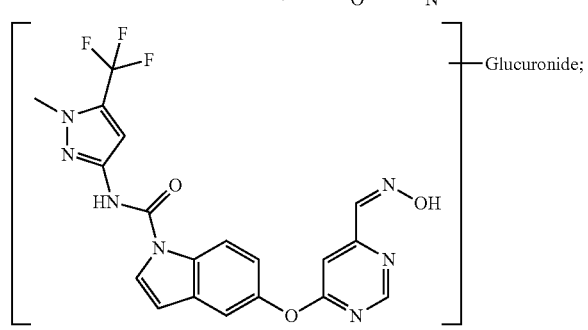

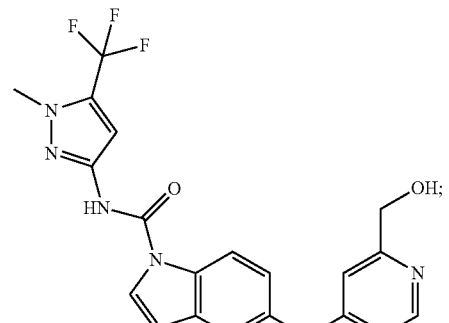

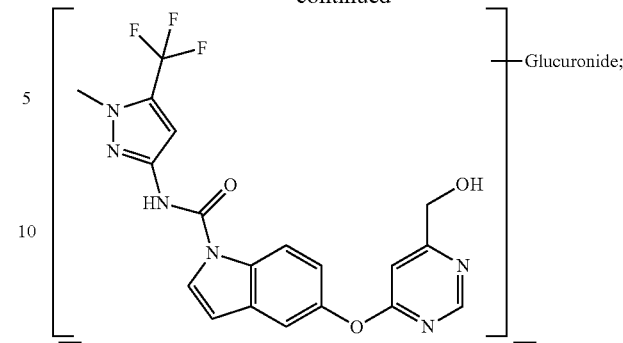

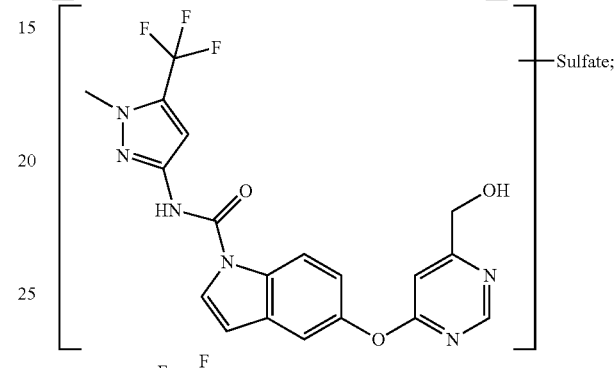

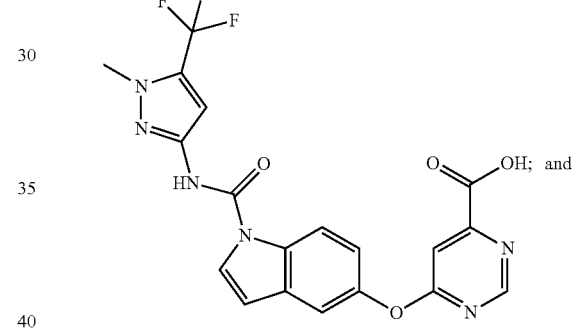

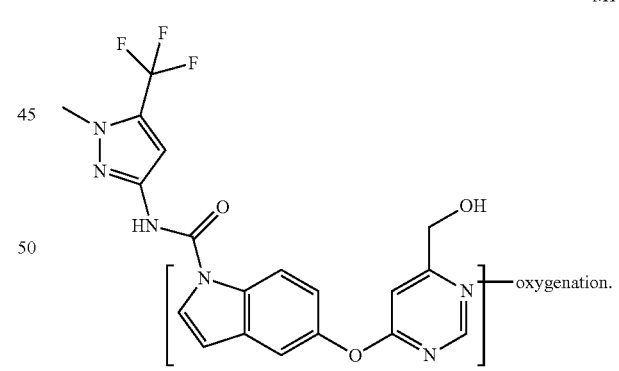

M18

Example 5—Preparation of N-(1-methyl-5-(trifluoromethyl)-1H-pyrazol-3-yl)-5-((6-((methylamino)methyl)pyrimidin-4-yl)oxy)-1H-indole-1-carboxamide (HCl Salt) Form A In a 5-L 4-neck round-bottom flask equipped with a mechanical stirrer, nitrogen inlet adapter, thermometer, addition funnel, and cooling bath was placed N-(1-methyl-5-(trifluoromethyl)-1H-pyrazol-3-yl)-5-(6-((methylamino)methyl)pyrimidin-4-yloxy)-1H-indole-1-carboxamide (76.8 g, 172.4 mmol) and ethanol (1.5 L). The white slurry was stirred at 20° C. for 30 min and HCl, 1 N (157 ml, 157 mmol) was added rapidly (pH=5). An additional amount of HCl was added (2 g) to lower the pH to 4. The resulting white suspension was stirred at 23 for 2 h and diluted with MTBE (1.5 L). The two phase mixture was cooled to 0-5° C. and stirred at this temperature for 3 h. The solids were isolated by suction filtration, washed with cold MTBE (2×30 mL), and dried at 55-60° C. in the vacuum oven to afford N-(1-methyl-5-(trifluoromethyl)-1H-pyrazol-3-yl)-5-(6-((methylamino)methyl)pyrimidin-4-yloxy)-1H-indole-1-carboxamide hydrochloride (66.9 g, 81%) as a tan solid.

This form was crystalline by XRPD and the DSC. XRPD for Form A is shown in FIG. 1. DSC for Form A is shown in FIG. 2.

TABLE 5

Powder X-Ray Diffraction Peaks Modification Form A

| Angle 2-Theta ° | d value Angstrom | Intensity Count |
|---|---|---|
| 6.391 | 13.83086 | 35.5 |
| 8.6 | 10.28184 | 176 |
| 9.532 | 9.27869 | 30.7 |
| 10.333 | 8.56084 | 59.9 |
| 11.74 | 7.53827 | 149 |
| 12.691 | 6.97491 | 181 |
| 13.486 | 6.56551 | 55.4 |
| 14.767 | 5.99906 | 53.9 |
| 15.105 | 5.86554 | 59.7 |
| 15.767 | 5.62066 | 140 |
| 16.571 | 5.34982 | 171 |
| 16.973 | 5.22394 | 65.3 |
| 17.39 | 5.09955 | 451 |
| 17.986 | 4.9319 | 124 |
| 18.854 | 4.70665 | 118 |
| 19.427 | 4.56913 | 93.7 |
| 19.99 | 4.44181 | 146 |
| 20.472 | 4.33833 | 87.6 |
| 20.993 | 4.23179 | 124 |
| 22.593 | 3.9355 | 141 |
| 23.166 | 3.83956 | 193 |
| 24.012 | 3.70603 | 102 |
| 24.413 | 3.64613 | 150 |
| 25.212 | 3.53231 | 54.2 |
| 25.788 | 3.45472 | 168 |
| 26.174 | 3.4047 | 164 |
| 26.974 | 3.30548 | 173 |
| 27.245 | 3.27326 | 104 |
| 28.231 | 3.16108 | 54.1 |
| 32.809 | 2.72975 | 82.6 |
| 34.843 | 2.57491 | 47.6 |
| 38.831 | 2.31912 | 35.3 |

Example 6—Preparation of N-(1-methyl-5-(trifluoromethyl)-1H-pyrazol-3-yl)-5-((6-((methylamino)methyl)pyrimidin-4-yl)oxy)-1H-indole-1-carboxamide (HCl Salt) Form B Crystalline form B of the HCl salt of N-(1-methyl-5-(trifluoromethyl)-1H-pyrazol-3-yl)-5-((6-((methylamino)methyl)pyrimidin-4-yl)oxy)-1H-indole-1-carboxamide was obtained using the same procedure as in Example 5 above. Form B is a transient form that converts back to Form A.

This form was crystalline by XRPD and the DSC. XRPD for Form B is shown in FIG. 3. DSC for Form A is shown in FIG. 4.

TABLE 6

Powder X-Ray Diffraction Peaks Modification Form B

| 2 theta | Intensity |
|---|---|
| 8.4113 | 2029 |
| 8.836 | 579 |
| 12.6789 | 847 |
| 13.5686 | 251 |
| 15.7124 | 598 |
| 16.8248 | 573 |
| 17.3911 | 377 |
| 18.7462 | 251 |
| 20.4248 | 334 |
| 21.072 | 651 |
| 24.126 | 706 |
| 24.6518 | 455 |
| 25.2788 | 441 |
| 26.5327 | 289 |
| 27.726 | 116 |
| 35.4721 | 141 |

Example 7—Preparation of Crystalline N-(1-methyl-5-(trifluoromethyl)-1H-pyrazol-3-yl)-5-((6-((methylamino)methyl)pyrimidin-4-yl)oxy)-1H-indole-1-carboxamide Form A A single crystalline polymorph of Crystalline N-(1-methyl-5-(trifluoromethyl)-1H-pyrazol-3-yl)-5-((6-((methylamino)methyl)pyrimidin-4-yl)oxy)-1H-indole-1-carboxamide has been discovered thus far an dis identified as Form A. The polymorph is a triclinic crystal with P1 space group. Form A has been crystallized from solutions of methanol, THF, acetone, ethanol, acetonitrile, methylene chloride by evaporation method to yield polymorph A at concentrations of 1 mg/mL. Crystalline N-(1-methyl-5-(trifluoromethyl)-1H-pyrazol-3-yl)-5-((6-((methylamino)methyl)pyrimidin-4-yl)oxy)-1H-indole-1-carboxamide polymorph A has also been prepared by heat/cooling cycling utilizing a Crystal 16 at concentrations>5 mg/mL in all the above solvents listed above.

Polymorph A is highly crystalline by XRPD (FIG. 5) and the DSC (FIG. 6) trace is characterized by an exothermic event at ~195° C. This form has 0.6% weight loss on heating.

TABLE 7

Powder X-Ray Diffraction Peaks Modification A

| Angle °2θ | d value Å | Intensity % |
|---|---|---|
| 8.664 | 10.20635 | 42.3 |
| 16.595 | 5.34185 | 50.7 |
| 17.423 | 5.09005 | 100 |
| 18.017 | 4.92334 | 49.6 |
| 19.448 | 4.56429 | 48.0 |
| 20.002 | 4.43910 | 57.4 |
| 20.468 | 4.33905 | 42.5 |
| 21.071 | 4.21625 | 41.3 |
| 22.649 | 3.92599 | 58.8 |
| 23.215 | 3.83152 | 77.9 |
| 24.468 | 3.63800 | 59.1 |
| 25.839 | 3.44810 | 63.3 |

Example 8—Chemical Synthesis of N-(1-methyl-5-(trifluoromethyl)-1H-pyrazol-3-yl)-5-((6-((methylamino)methyl)pyrimidin-4-yl)oxy)-1H-indole-1-carboxamide

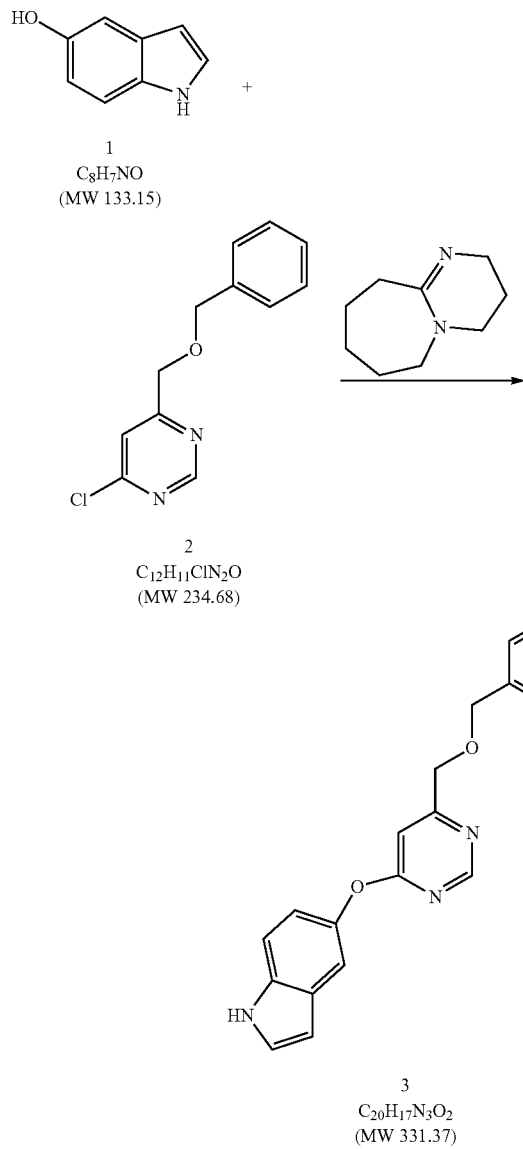

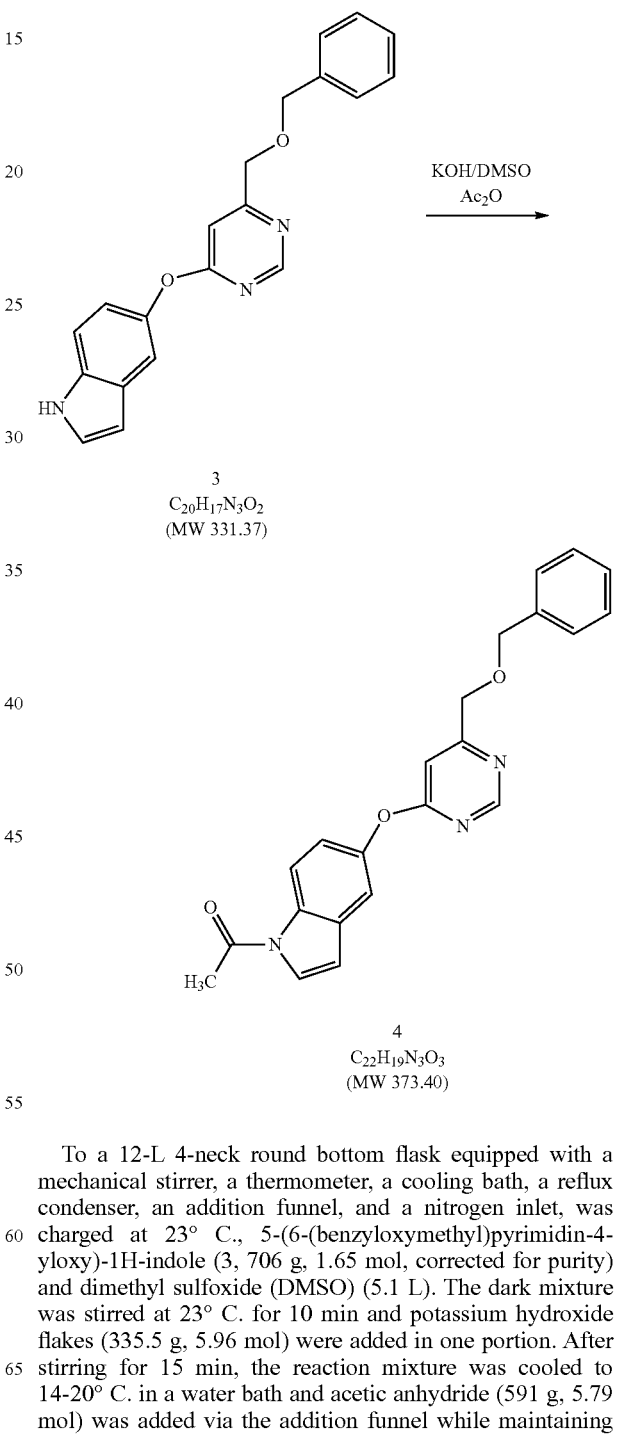

To a 5-L 4-neck round bottom flask equipped with a mechanical stirrer, a thermometer, a heating mantle, a reflux condenser and a nitrogen inlet, was charged at 23° C., 5-hydroxyindole (1, 257.7 g, 1.94 mol) and acetonitrile (3 L). The dark mixture was stirred for 15 min. The internal temperature decreased to 15° C. In one portion, 4-(benzyloxymethyl)-6-chloropyrimidine (2, 386.6 g, 1.65 mol) was added. The flask was rinsed with acetonitrile (2×50 mL) which was added to the batch. The reaction mixture was warmed to 20° C., and 1,8-diazabicyclo[5.4.0]undec-7-ene (DBU) (380 g, ~376 mL, 2.5 mol) was added drop wise via an addition funnel over 25 min. The reaction mixture turned from a yellow-tan slurry into a dark solution and was heated at an internal temperature of 64-66° C. for 18 h. The reaction mixture was concentrated at a bath temperature of 50° C. to remove the majority of the acetonitrile. The residue was diluted with methyl t-butyl ether (MTBE)(1.5 L) and water (1.2 L). The layers were separated and the aqueous layer was extracted with MTBE (2×500 mL). The organic layers were combined and washed with water (800 mL), 0.5 N sodium hydroxide solution (800 mL) and a mixture of saturated sodium chloride solution (500 mL) and water (100 mL). The organic layer was concentrated at a bath temperature of 50° C. to afford crude 5-(6-(benzyloxymethyl)pyrimidin-4-yloxy)-1H-indole (3, 707 g, >100%) as a dark viscous liquid which was used in the next step without further purification.

To a 12-L 4-neck round bottom flask equipped with a mechanical stirrer, a thermometer, a cooling bath, a reflux condenser, an addition funnel, and a nitrogen inlet, was charged at 23° C., 5-(6-(benzyloxymethyl)pyrimidin-4-yloxy)-1H-indole (3, 706 g, 1.65 mol, corrected for purity) and dimethyl sulfoxide (DMSO) (5.1 L). The dark mixture was stirred at 23° C. for 10 min and potassium hydroxide flakes (335.5 g, 5.96 mol) were added in one portion. After stirring for 15 min, the reaction mixture was cooled to 14-20° C. in a water bath and acetic anhydride (591 g, 5.79 mol) was added via the addition funnel while maintaining the temperature below 25° C. The temperature was kept below 25° C. and the reaction was stirred for 10 h. The reaction mixture was diluted with MTBE (3 L) and cooled to 10-15° C. Water (2.5 L) was added slowly over 15 min while maintaining the batch temperature below 25° C. The resulting tan mixture was stirred at 21° C. for 1 h and allowed to stand overnight. The aqueous layer was extracted with MTBE (3×1.2 L). The combined organic layers (~7 L) were washed with saturated sodium bicarbonate solution (1.7 L), water (3×1.5 L) and saturated sodium chloride (1.5 L). Concentration under reduced pressure at 50° C. gave dark brown viscous liquid (604 g). The crude material was purified by filtration through a silica gel column, eluting with MTBE to afford crude 1-(5-(6-(benzyloxymethyl)pyrimidin-4-yloxy)-1H-indol-1-yl)ethanone (4, 593 g, 96%) as an orange oil which was used in the next step without further purification.

mixture was heated to 70° C. for 20 h. After cooling to 23° C., the reaction was diluted with toluene (400 mL) and added slowly to a mixture of sodium bicarbonate (280 g, 3.33 mol), water (1.2 L), and toluene (200 mL). The temperature was maintained below 24° C. during the addition. The resulting yellow slurry was stirred at 23° C. overnight (pH=6). The solids were filtered with suction, washed with water (100 mL), and toluene (100 mL) and dried at 55-60° C. in the vacuum oven. The resulting dried material (61.3 g) was purified by stirring in ethyl acetate (185 mL) at 50° C. for 30 min followed by 23° C. for 6 h and drying as above to afford 1-(5-(6-(hydroxymethyl)pyrimidin-4-yloxy)-1H-indol-1-yl)ethanone (5, 37.4 g, 58%) as a tan solid.

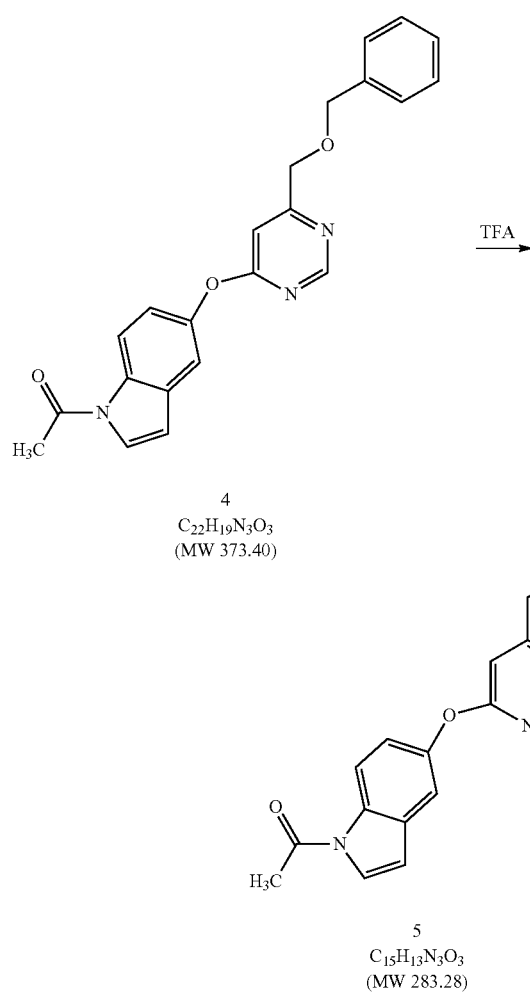

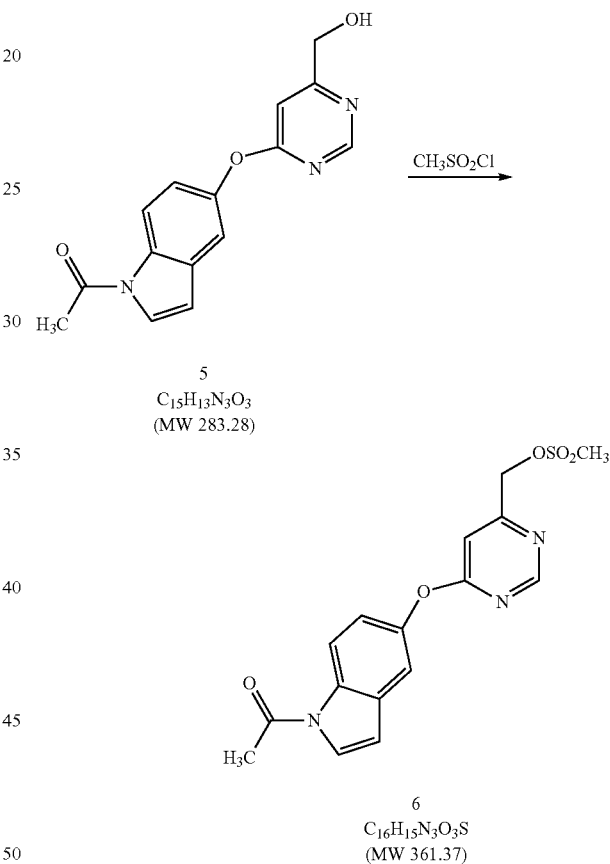

To a 1-L 4-neck round bottom flask equipped with a mechanical stirrer, a thermometer, a reflux condenser, a heating mantle, and a nitrogen inlet, was charged 1-(5-(6-(benzyloxymethyl)pyrimidin-4-yloxy)-1H-indol-1-yl)ethanone (4, 100 g, 267.8 mmol) and toluene (40 mL). The solution was stirred at 23° C. for 10 min and trifluoroacetic acid (368.4 g, 3.23 mol) was added rapidly. The batch temperature increased to 45° C. during the addition. The To a 5-L 4-neck round bottom flask equipped with a mechanical stirrer, a thermometer, a cooling bath, an addition funnel, and a nitrogen inlet, was charged 1-(5-(6-(hydroxymethyl)pyrimidin-4-yloxy)-1H-indol-1-yl)ethanone (5, 134.2 g, 473.7 mmol)(93% purity), THF (2.4 L), and 4-dimethylaminopyridine (DMAP) (6 g, 49 mmol). After stirring for 15 min, triethylamine (98 g, 968.4 mmol) was added in one portion and the resulting slurry was cooled below 5° C. Methanesulfonyl chloride (89 g, 777 mmol) was added over 25 min while maintaining the temperature below 7° C. The tan suspension was stirred at 0-5° C. for 1.5 h. Water (250 mL) was added and the batch was warmed to 23° C. The reaction mixture was concentrated under reduced pressure (bath temperature=38° C.) and the residue was diluted with ethyl acetate (500 mL). The mixture was concentrated again and the residue was diluted with ethyl acetate (1 L) and water (300 mL). After stirring for 5 h at 23° C., the resulting solids were filtered with suction, washed with a 1:1 mixture of ethyl acetate and water (2×60 mL) and dried under reduced pressure at 40-50° C. to constant weight to give 6-(1-acetyl-1H-indol-5-yloxy)pyrimidin-4-yl)methyl methanesulfonate (6, 142.2 g, 83%) as a tan solid. The mesylate (7) can be further purified by stirring in ethyl acetate at 23° C. for 18 h.

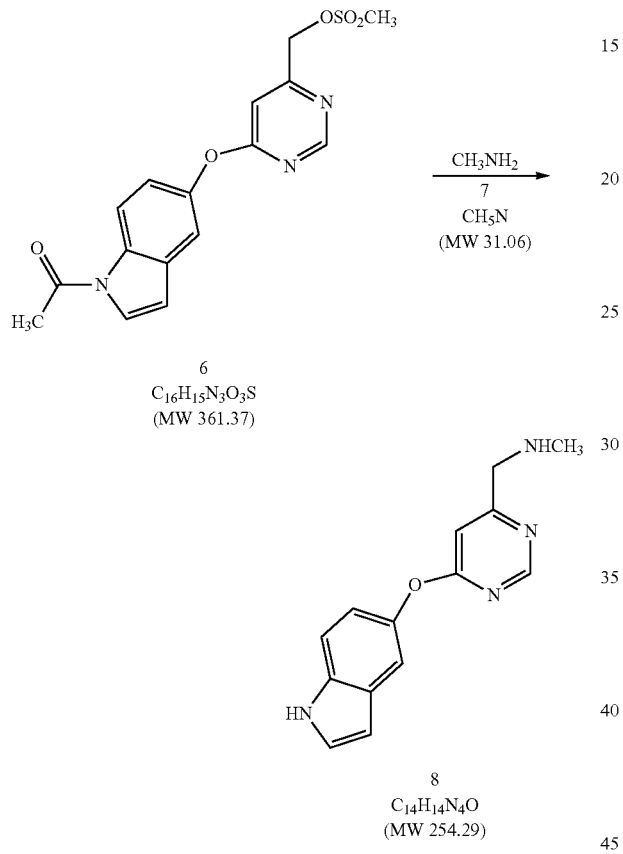

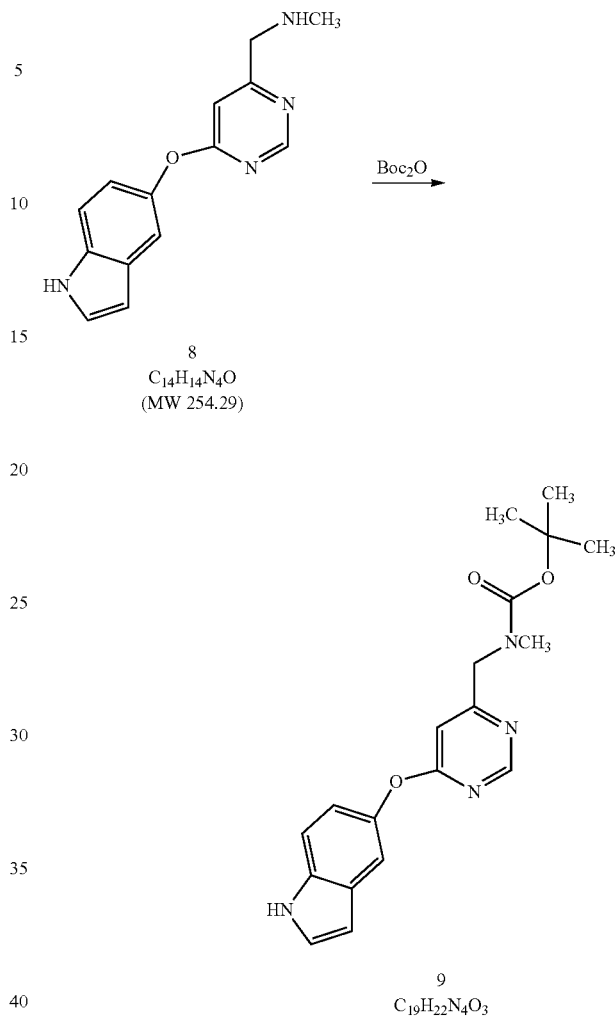

To a 5-L 4-neck round bottom flask equipped with a mechanical stirrer, a thermometer, a water bath, and a nitrogen inlet adapter, was charged 6-(1-acetyl-1H-indol-5-yloxy)pyrimidin-4-yl)methyl methanesulfonate (6, 118.5 g, 328.2 mmol) (95% purity) and methylamine, 2 M in THF (7, 2.04 L, 4 mol) at 23° C. The clear orange solution was stirred at 23° C. for 8 h. The reaction mixture was concentrated under reduced pressure at 40° C. and the residue was diluted with ethyl acetate (1.2 L). At 20° C. a solution of sodium carbonate (90 g) in water (500 mL) was added. The organic layer was separated and washed with water (400 mL) and saturated sodium chloride (400 mL). The organic layer was concentrated under reduced pressure at 40° C. and the resulting solids were stirred in isopropyl acetate (250 mL) at 40° C. for 1 h and then at 23° C. for 6 h. The solids were isolated by suction filtration, washed with isopropyl acetate (2×15 mL) and dried under reduced pressure at 45° C. to give 1-(6-(1H-indol-5-yloxy)pyrimidin-4-yl)-N-methylmethanamine (8, 66.4 g, 80%) as a tan solid.

To a 3-L 4-neck round bottom flask equipped with a thermometer, heating mantle, nitrogen inlet, reflux condenser and addition funnel was charged at room temperature 1-(6-(1H-indol-5-yloxy)pyrimidin-4-yl)-N-methylmethanamine (8, 33.2 g, 130.561 mmol) and dichloromethane (1.125 L). The hazy yellow solution was stirred at 23° C. for 10 min. To this mixture was added in one portion as a solid di-tert-butyl dicarbonate (28.210 g, 129.255 mmol) and the solution was stirred at 23° C. for 12 h. The cloudy orange solution was filtered through filter paper and concentrated (38° C./300 mm) to an orange gum (62.9 g). Ethyl acetate (0.4 L) was added and the solution was washed with 15% aqueous ammonia (125 mL) and saturated sodium chloride (125 mL) and dried over sodium sulfate. After filtration, the solution was concentrated on the rotary evaporator at 40° C./100 mm to a dark orange oil (46.3 g). The oil was stirred in 1:1 MTBE/Heptanes (80 mL) for 12 h and the resulting yellow solids were filtered and washed with 2:1 Heptanes/MTBE (2×55 mL) and dried in the vacuum oven at 50° C. overnight to afford tert-butyl (6-(1H-indol-5-yloxy)pyrimidin-4-yl)methyl(methyl)carbamate (9, 33.8 g, 71%).

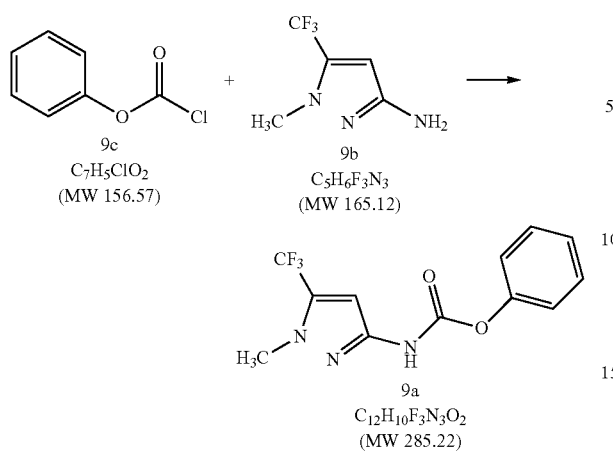

In a 5-L 4-neck round-bottom flask equipped with a mechanical stirrer, nitrogen inlet, reflux condenser, and thermometer was placed phenyl carbonochloridate (9c, 94 mL, 0.75 mol, 117.5 g) and THF (2000 mL). The solution was heated at reflux (80° C. internal temperature) and 1-methyl-5-(trifluoromethyl)-1H-pyrazol-3-amine (9b, 82.5 g, 499.649 mmol) in THF (500 mL) was added drop wise over 30 min. The clear orange solution was heated at reflux for 16 h and concentrated on the rotary evaporator (40° C., 120 mm). The resulting white solid was stirred in heptanes (500 mL) for 30 min, filtered, washed with heptanes, and dried at 50° C. in the vacuum oven to give phenyl 1-methyl-5-(trifluoromethyl)-1H-pyrazol-3-ylcarbamate (9a, 121.9 g, 85%) as a white solid.

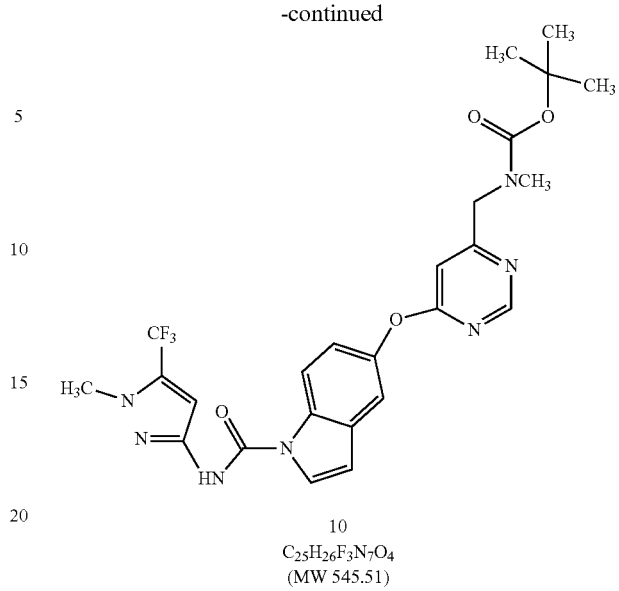

Sodium hydride (60% oil dispersion) (38.145 g, 953.717 mmol) was suspended in THF (1375 mL) and cooled to 0° C. in an ice bath. A solution of tert-butyl (6-(1H-indol-5-yloxy)pyrimidin-4-yl)methyl(methyl)carbamate (9, 130.000 g, 366.814 mmol) in THF (1375 mL) was added drop wise over 90 min keeping the temperature below 5° C. The suspension turned from gray to orange. After stirring for 0.5 h at 0° C., a solution of phenyl 1-methyl-5-(trifluoromethyl)-1H-pyrazol-3-ylcarbamate (9a, 115.086 g, 403.495 mmol) in THF (500 mL) was added drop wise over 60 min. The mixture was stirred for 1 h at 0° C. at which time it had become a dark brown suspension (some solids present). Ethyl acetate (3500 mL) and saturated ammonium chloride (1000 mL) were added at at 0° C. After stirring for several minutes, the layers were separated and the organic layer was washed with saturated sodium chloride (1500 mL) and dried over sodium sulfate. The ethyl acetate solution was filtered through Silica Gel 60 (230-400 mesh) and Celite on a Buchner funnel and the filtrate was concentrated to a wet beige solid (oil from the NaH). MTBE (625 mL) was added and the mixture was stirred for 60 min. The resulting solid was filtered, washed with MTBE (2×250 mL) and dried in the vacuum oven at 50° C. to afford tert-butyl methyl((6-(1-(1-methyl-5-(trifluoromethyl)-1H-pyrazol-3-ylcarbamoyl)-1H-indol-5-yloxy)pyrimidin-4-yl)methyl)carbamate (10) (150.7 g, 75%) as an off-white solid.

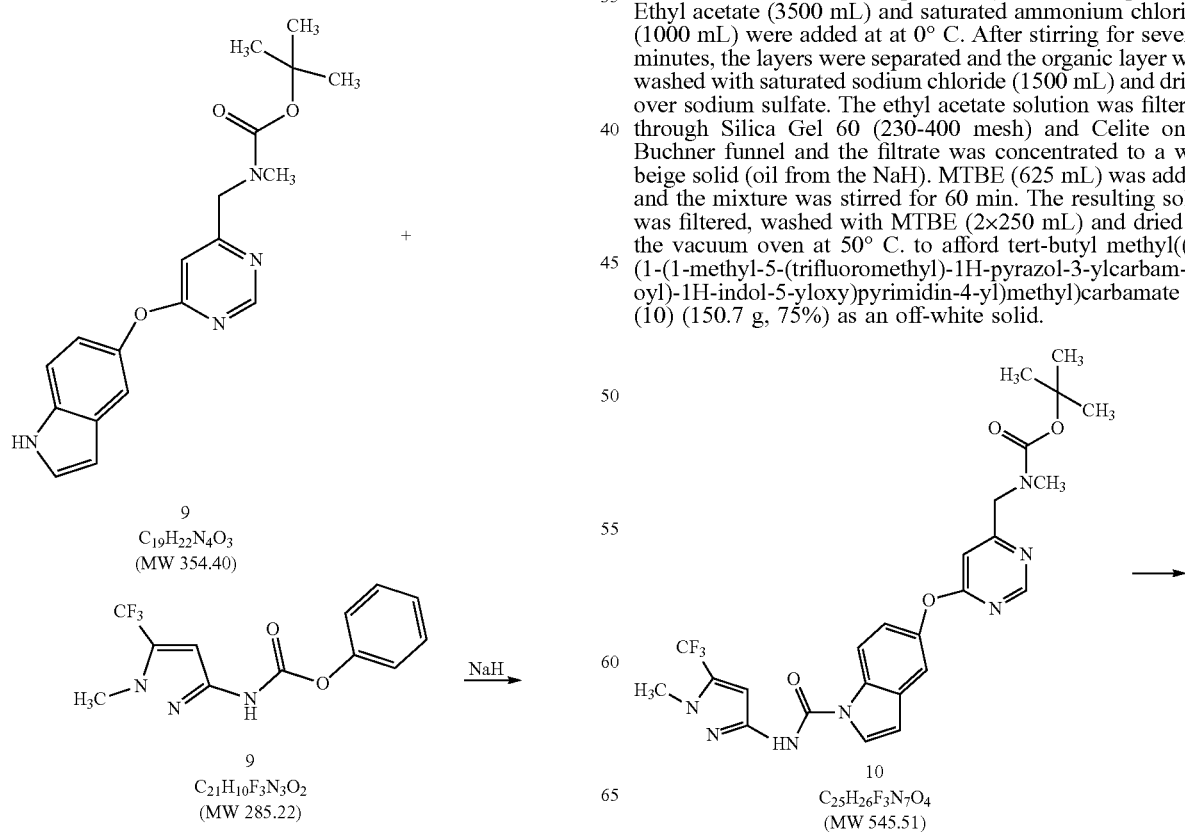

-continued

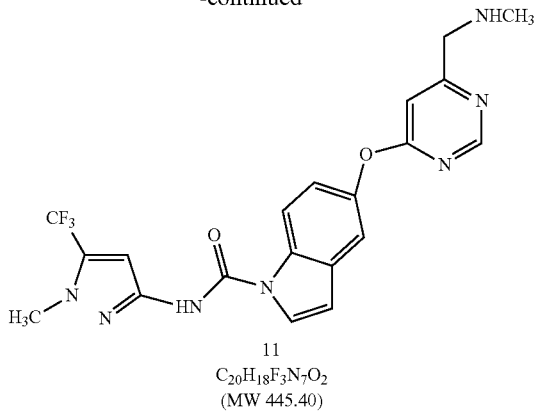

11
$C_{20}H_{18}F_3N_7O_2$
(MW 445.40)

In a 5-L 4-neck round-bottom flask equipped with a mechanical stirrer, nitrogen inlet adapter, thermometer, and addition funnel was placed tert-butyl methyl((6-(1-(1-methyl-5-(trifluoromethyl)-1H-pyrazol-3-ylcarbamoyl)-1H-indol-5-yloxy)pyrimidin-4-yl)methyl)carbamate (10)(180 g, 330 mmol) and dichloromethane (2880 ml). The solid dissolved to form a clear orange solution and this was cooled to below 5° C. At this point, 2,2,2-trifluoroacetic acid (396 ml, 5.34 mol) was added drop wise keeping the temperature below 5° C. The time of the addition was ~1.5 h. The cooling bath was removed and the solution was allowed to warm to 22° C. and stir for 5.5 h. The solution was slowly added to a solution of sodium carbonate (792 g) in water (3600 mL) (T=10-15° C.). A slight exotherm was observed and a white suspension formed. This was allowed to stir overnight. The suspension was filtered and the solids were washed with water (2×1500 mL). After air drying on the funnel for several hours, the solids were dried overnight in the vacuum oven at 50° C. The dried solids (356.7 g) were allowed to stir in water (3600 mL) overnight, filtered, washed with water (3×500 mL) and dried as above to afford N-(1-methyl-5-(trifluoromethyl)-1H-pyrazol-3-yl)-5-(6-((methylamino)methyl)pyrimidin-4-yloxy)-1H-indole-1-carboxamide (11, 120 g, 80%) as an off-white solid.

Example 9 KDR Protein Kinase Activities
Measured by the LanthaScreen TR-FRET Method A generic assay set-up has been run at room temperature on a liquid handling robot. To the assay plates containing 50 nL compound or control solutions, 4.5 µL of ATP mix (20 mM Tris-HCl pH7.4, 1 mM DTT, 0.025% Tween20, 0.01 mM Na$_3$VO$_4$, 10 mM MgCl$_2$, 1 mM MnCl$_2$, and 4 µM ATP) were added per well. Subsequently, 4.5 µL of enzyme-substrate mix (20 mM Tris-HCl pH7.4, 1 mM DTT, 0.025% Tween20, 0.01 mM Na$_3$VO$_4$, 10 mM MgCl$_2$, 1 mM MnCl$_2$, 0.5% BSA, 100 nM fluorescein labeled poly(EAY), and 0.76 nM KDR (GST-KDR(807-1356), internally produced recombinant protein) were added.

The final reaction volume is 9.05 µL with final reagent concentrations of 20 mM Tris-HCl pH7.4, 1 mM DTT, 0.025% Tween20, 0.01 mM Na$_3$VO$_4$, 10 mM MgCl$_2$, 1 mM MnCl$_2$, including a generic concentration of 2 µM ATP, 50 nM of substrate fluorescein labeled poly(EAY), and 0.38 nM enzyme.

After 1 hour of incubation the kinase reactions have been stopped by the addition of 4.5 µL of stop solution (20 mM Tris-HCl pH7.4, 1 mM DTT, 0.025% Tween20, 0.01 mM Na$_3$VO$_4$, 50 mM EDTA) immediately followed by 4.5 µL of antibody solution (20 mM Tris-HCl pH7.4, 1 mM DTT, 0.025% Tween20, 0.01 mM Na$_3$VO$_4$, 1.72 µg/ml Tb-PY20).

After an incubation time of 45 min in the dark, the plates were transferred into a fluorescence reader and counted in time resolved fluorescence mode (settings according to the reagent supplier's recommendation). The effect of compound on the enzymatic activity was obtained from end point measurement.

TABLE 4

$IC^{50}$ Values for the Examples

| Example | $IC^{50}$ |
|---------|-----------|
| 1 | <1 nm |
| 2 | 20 nm |
| 3 | <1 nm |

What is claimed:
1. A method for treating macular degeneration, diabetic retinopathy, retinopathy, or retinitis pigmentosa in a subject in need thereof, wherein said method comprises administering to the subject a compound selected from the group consisting of:

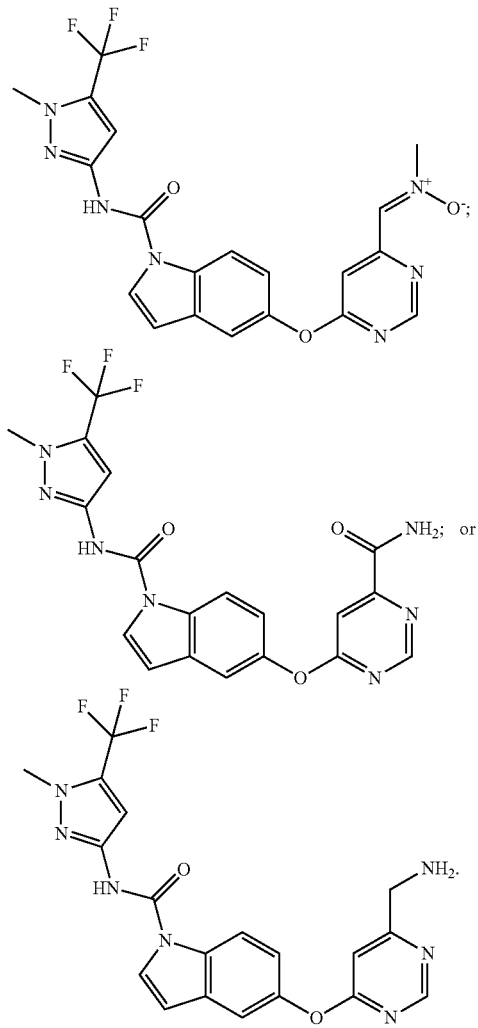

2. The method of claim 1, wherein the subject has macular degeneration.

* * * * *